United States Patent
Hu et al.

(10) Patent No.: US 11,518,726 B2
(45) Date of Patent: Dec. 6, 2022

(54) SYNTHESIS OF BICYCLO[2.2.2]OCTANE DERIVATIVES

(71) Applicant: Eastman Chemical Company, Kingsport, TN (US)

(72) Inventors: Yue Rachel Hu, Kingsport, TN (US); Robert Thomas Hembre, Johnson City, TN (US); Gerald Charles Tustin, Kingsport, TN (US); Zhufang Liu, Kingsport, TN (US); Steven J. Adams, Gray, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/754,206

(22) PCT Filed: Oct. 10, 2018

(86) PCT No.: PCT/US2018/055138
§ 371 (c)(1),
(2) Date: Apr. 7, 2020

(87) PCT Pub. No.: WO2019/075004
PCT Pub. Date: Apr. 18, 2019

(65) Prior Publication Data
US 2020/0270191 A1    Aug. 27, 2020

Related U.S. Application Data

(60) Provisional application No. 62/570,866, filed on Oct. 11, 2017.

(51) Int. Cl.
| | | |
|---|---|---|
| *C07C 29/60* | (2006.01) | |
| *C07C 45/50* | (2006.01) | |
| *C07C 51/16* | (2006.01) | |
| *C07C 67/36* | (2006.01) | |
| *C07C 209/16* | (2006.01) | |
| *C07C 231/02* | (2006.01) | |
| *C07C 263/10* | (2006.01) | |
| *C07C 29/48* | (2006.01) | |
| *C07C 69/013* | (2006.01) | |
| *C07C 51/12* | (2006.01) | |
| *C07C 61/13* | (2006.01) | |
| *C07C 31/27* | (2006.01) | |
| *C07C 211/19* | (2006.01) | |
| *C07C 215/20* | (2006.01) | |
| *C07C 213/02* | (2006.01) | |

(52) U.S. Cl.
CPC .............. *C07C 29/60* (2013.01); *C07C 29/48* (2013.01); *C07C 31/278* (2013.01); *C07C 45/50* (2013.01); *C07C 51/12* (2013.01); *C07C 51/16* (2013.01); *C07C 61/13* (2013.01); *C07C 67/36* (2013.01); *C07C 69/013* (2013.01); *C07C 209/16* (2013.01); *C07C 211/19* (2013.01); *C07C 213/02* (2013.01); *C07C 215/20* (2013.01); *C07C 231/02* (2013.01); *C07C 263/10* (2013.01); *C07C 2602/44* (2017.05)

(58) Field of Classification Search
CPC combination set(s) only.
See application file for complete search history.

(56) References Cited

U.S. PATENT DOCUMENTS

| | | |
|---|---|---|
| 3,081,334 A | 3/1963 | Kauer |
| 3,228,984 A | 1/1966 | Humber |
| 3,255,254 A | 6/1966 | Kauer |
| 3,256,241 A | 6/1966 | Watson |
| 3,301,827 A | 1/1967 | Martin |
| 3,337,498 A | 8/1967 | Hogsed et al. |
| 3,367,941 A | 2/1968 | Gregory et al. |
| 3,533,594 A | 10/1970 | Segmüller |
| 3,546,290 A | 12/1970 | Kauer |
| 4,020,141 A | 4/1977 | Quinn et al. |
| 4,355,080 A | 10/1982 | Zannucci |
| 4,448,998 A | 5/1984 | King |
| 4,486,561 A | 12/1984 | Chung et al. |
| 5,707,667 A | 1/1998 | Galt et al. |

(Continued)

FOREIGN PATENT DOCUMENTS

| | | | |
|---|---|---|---|
| CN | 106748704 | * 5/2017 | .......... C07C 29/149 |
| FR | 1 374 693 | 10/1964 | |

(Continued)

OTHER PUBLICATIONS

Pritchard ("Heterogeneous and homogeneous catalysis for the hydrogenation of carboxylic acid derivatives: history, advances and future directions" 2015, 44, p. 3808-3833) (Year: 2015).*

Hydrogenation (Wikipedia entry, downloaded from https://en.wikipedia.org/wiki/Hydrogenation on Jan. 25, 2021) (Year: 2021).*

Adcock ("Polar Substituent Effects on 19F Chemical Shifts of Aryl and Vinyl Fluorides: A Fluorine-19 Nuclear Magnetic Resonance Study of Some 1,1-Difluoro-2-(4-substituted-bicyclo[2.2.2]oct-1-yl)ethenes"J. Org. Chem. 50, 1985, p. 1079-1087) (Year: 1985).*

Kumar ("Synthesis, Characterization, and Chemistry of Bridgehead-Functionalized Bicyclo[2.2.2]octanes: Reactions at Neopentyl Sites"J. Org. Chem. 49, 1984, p. 665-670) (Year: 1984).*

(Continued)

*Primary Examiner* — Amy C Bonaparte
(74) *Attorney, Agent, or Firm* — C. Stuart Everett; Tammye L. Taylor Polk

(57) ABSTRACT

Provided is a process for the preparation of certain 1,4-bicyclo[2.2.2]octane derivatives. The new synthetic procedure involves treating 1,4-dimethylene cyclohexane with an oxidizing agent in the presence of a transition metal catalyst to afford an oxo-substituted bicyclo[2.2.2]octane species. This intermediate structure can then be further derivatized. The processes of this disclosure thus affords a novel and simplified means for the commercial production of a wide variety of bicyclo[2.2.2]octane derivatives.

18 Claims, No Drawings

(56) References Cited

U.S. PATENT DOCUMENTS

| | | | |
|---|---|---|---|
| 6,183,848 | B1 | 2/2001 | Turner et al. |
| 6,368,532 | B1 | 4/2002 | Otoshi et al. |
| 6,649,600 | B1 | 11/2003 | Kiesman et al. |
| 6,921,736 | B1 | 7/2005 | Nolan et al. |
| 7,132,499 | B2 | 11/2006 | Tobita et al. |
| 7,781,562 | B2 | 8/2010 | Crawford et al. |
| 9,082,912 | B2 | 7/2015 | Levy |
| 9,328,050 | B1 | 5/2016 | Boppana et al. |
| 2006/0004151 | A1 | 1/2006 | Shaikh et al. |
| 2008/0053512 | A1 | 3/2008 | Kawashima |
| 2010/0324207 | A1 | 12/2010 | Sturzel et al. |
| 2011/0091705 | A1 | 4/2011 | Shih et al. |
| 2014/0087990 | A1 | 3/2014 | Kitamura et al. |
| 2016/0039780 | A1 | 2/2016 | Shi et al. |

FOREIGN PATENT DOCUMENTS

| | | |
|---|---|---|
| GB | 1 024 487 | 3/1966 |
| JP | 06 032882 A | 2/1994 |
| WO | WO 00 47635 A1 | 8/2000 |
| WO | WO 2006 128184 A2 | 11/2006 |
| WO | WO 2018 075301 A1 | 4/2018 |

OTHER PUBLICATIONS

Wikipedia entry for "Chromite", downloaded from https://en.wikipedia.org/wiki/Chromite on Dec. 22, 2021 (Year: 2021).*

Liu ("Surface synergistic effect in well-dispersed Cu/MgO catalysts for highly efficient vapor-phase hydrogenation of carbonyl compounds" Catal. Sci. Technol. 2015, 5, p. 3960-3969) (Year: 2015).*

Gong ("Copper nanoparticles socketed in situ into copper phyllosilicate nanotubes with enhanced performance for chemoselective hydrogenation of esters" Chem. Commun. 2017, 53, p. 6933-6936) (Year: 2017).*

Adkins, Homer and Wojcik, Bruno; "Hydrogenation of Amides to Amines"; Journal of the American Chemical Society—Communications to the Editor; p. 247; 1934.

AGFA, Power by Technology; "UNIQOAT—The Single-Layer Backsheet"; 2 pages; Jun. 2018; retrieved from website: http://www.agfa.com/specialty_products/solutions/solar-pv-backsheet/uniqoat.

Bailey, William J. and Golden, Harold R.; "Cyclic Dienes. I. 1,2-Dimethylenecyclohexane"; Journal of the American Chemical Society; pp. 4780-4782; Oct. 5, 1953.

Baleizão, Carlos et al.; "Oxime Carbapalladacycle Covalently Anchored to High Surface Area Inorganic Supports or Polymers as Heterogeneous Green Catalysts for the Suzuke Reaction in Water"; Journal of Organic Chemistry, 69; pp. 439-446; 2004.

Bedford, Robin B. et al.; "Silica-supported imine palladacycles-recyclable catalysts for the Suzuki reaction?"; Journal of Organometallic Chemistry, 633; pp. 173-181; 2001.

Carr, N. et al.; "A Comparison of the Properties of Some Liquid Crystal Materials Containing Benzene, Cyclohexane, and Bicyclo[2.2.2]octane Rings"; Molecular Crystals and Liquid Crystals, vol. 66; pp. 267-282; 1981.

Chang, Hexi, et al.; "Convenient One-Pot Preparation of Dimethyl Bicyclo[2.2.2]octane-1,4-dicarbolylate, a Key Intermediate for a Novel Adenosine $A_1$ Receptor Antagonist"; Synthetic Communications, vol. 37; pp. 1267-1272; 2007.

Clark, Jim; "Making Amines"; 6 pages; 2004, modified Mar. 2016; retrieved from website: https://www.chemguide.co.uk/organicprops/amines/preparation.html.

Corma, Avelino et al.; "A periodic mesoporous organosilica containing a carbapalladacycle complex as heterogeneous catalyst for Suzuki cross-coupling"; Journal of Catalysis, 229; pp. 322-331; 2005.

Corma, Avelino et al.; "An imidazolium ionic liquid having covalently attached an oxime carbapalladacycle complex as ionophilic heterogeneous catalysts for the Heck and Suzuki-Miyaura cross-coupling"; Tetrahedron, 60; pp. 8553-8560; 2004.

Dewar, Michael J. S. and Goldberg, Ronald S.; "The Role of ρ-Phenylene Groups in Nematic Liquid Crystals"; Journal of the American Chemical Society, 92:6; pp. 1582-1586; Mar. 25, 1970.

Dotrong, M. et al.; "Synthesis, Characterization, and Properties of Colorless Rigid-Rod Poly(benzobisthiazole) Derived from Bicyclo[2.2.2]octane"; Journal of Polymer Science: Part A: Polymer Chemistry, vol. 32; pp. 2953-2960; 1994.

Fehling; "Ueber die Bernsteinsäure und ihre Verbindungen"; Justus Liebigs Annalen der Chemie, 49; pp. 154-212; 1844 (Original Language).

Ferreira, Arthur Batista et al.; "Tin-Catalyzed Esterification and Transesterification Reactions: A Review"; International Scholarly Research Network (ISRN Renewable Energy), vol. 2012, Article ID 142857, 13 pages.

Friberg, Annika et al.; "Efficient bioreduction of bicyclo[2.2.2]octane-2,5-dione and bicyclo[2.2.2]oct-7-ene-2,5-dione by genetically engineered *Saccharomyces cerevisiae*"; Organic & Biomolecular Chemistry, 4; pp. 2304-2312; 2006.

Geivandov, R. KH et al.; "New synthesis of 1,4-dihydroxybicyclo[2.2.2]octane" Zhurnal Organicheskoi Khimii; pp. 218-219; Jan. 1, 1979 (Original Language).

Gu, Xin et al.; "Discovery of 4-heteroarylbicyclo[2.2.2]octyltriazoles as potent and selective inhibitors of 11β-HSD1: Novel therapeutic agents for the treatment of metabolic syndrome"; Bioorganic & Medicinal Chemistry Letters 15; pp. 5266-5269; 2005.

Guha, P. C.; "Para-Brückenbildung beim Succinylo-bernsteinsäure-äthylester, I. Mitteil.: Bildung von Bicyclo-[1.2.2]-heptan-, Bicyclo[2.2.2]octan- und Bicyclo-[3.2.2]-nonan-Systemen"; Chemische Berichte, vol. 72, Part 2; pp. 1359-1373; 1939 (Original Language).

Gürbüz, Nevin et al.; "Surface Modification of Inorganic Oxide Particles with a Carbene Complex of Palladium: A Recyclable Catalyst for the Suzuki Reaction"; Journal of Inorganic and Organometallic Polymers, vol. 14, No. 2; p. 149; Jun. 2004.

Guyer, von A. et al.; "197. Über die katalytische Reduktion aliphatischer Carbonsäureamide"; Helv. Chim. Acta, Volumen XXXVIII; pp. 1649-1654; 1955 (Original Language).

Harruna, Issifu I. and Polk, Malcolm B.; "Thermotropic Copolyesters. II. Synthesis and Characterization of Copolyesters Containing the Bicyclo[2.2.2]oct-2-ene Mesogenic Unit"; Journal of Polymer Science: Part A: Polymer Chemistry, vol. 26; pp. 2171-2182; 1988.

Harruna, Issifu I. and Polk, Malcolm B.; "Thermotropic Homopolyester. I. Synthesis and Characterization of Homopolyesters Containing the Mesogenic Unit, Bicyclo[2.2.2]oct-2-ene"; Journal of Polymer Science: Part A: Polymer Chemistry, vol. 28; pp. 285-298; 1990.

Harruna, Issifu I. and Polk, Malcolm B.; "Thermotropic copolyesters: 3. Synthesis and characterization of liquid crystal copolyesters containing the bicyclo[2.2.2]octane mesogenic unit"; Polymer Communications, vol. 32, No. 2; pp. 39-41; 1991.

He, De-Hua et al.; "Hydrogenation of Carboxylic Acids Using Bimetallic Catalysts Consisting of Group 8 to 10 and Group 6 or 7 Metals"; Tetrahedron Letters, vol. 36, No. 7; pp. 1059-1062; 1995.

Hirosawa, Chitaru et al.; "Hydrogenation of Amides by the Use of Bimetallic Catalysts Consisting of Group 8 to 10 and Group 6 or 7 Metals" Tetrahedron Letters, vol. 37, No. 37; pp. 6749-6752; 1996.

Holtz, Hans D. and Stock, Leon M.; "The Preparation of 1-Carobyx-4-substituted Bicyclo [2.2.2]octanes"; Journal of the American Chemical Society, vol. 86; pp. 5183-5188; Dec. 5, 1964.

Humber, L. G. et al.; "Agents Affecting Lipid Metabolism XIII. The Synthesis of 1,4-disubstituted Bicyclo[2.2.2]Octane Derivatives"; Candian Journal of Chemistry, vol. 42; pp. 2852-2861; 1964.

Kauer, J. C. et al; "Bridgehead-Substituted Bicyclo[2.2.2]octanes. I. Addition of Ethylene to Cyclohexa-1,3-diene-l,4-dicarboxylic Acid Derivatives"; Journal of Organic Chemistry, vol. 30; pp. 1431-1436; May 1965.

Kopecký, Jan and Šmejkal, Jaroslav; "Synthesis of Bridgehead Chloro- Bromo- and Iodobicyclo[2.2.2]octanes"; Collection Czechoslovak Chemical Communications, vol. 45; p. 2965; 1980.

Kopecký, Jan et al.; "Synthesis of Bridgehead Bicyclo[2.2.2]octanols"; Collection of Czechoslovak Chemical Communications, vol. 46; pp. 1370-1375; 1981.

(56) References Cited

OTHER PUBLICATIONS

Kopecký, Jan and Šmejkal, Jaroslav; "The Synthesis of 1,4-Dihydroxy- and 1,4-Dihalogenobicyclo[2.2.2]octanes"; Tetrahedron Letters, No. 40; pp. 3889-3891; Jul. 1967.

Kuehne, ME. E. and Lambert, B. F.; "1,4-Dihydrobenzoic Acid [2,5-Cyclohexadiene-1-carboxylic acid]"; Organic Synthesis, Coll., vol. 43; p. 22; 1963.

Lemouchi, Cyprien et al.; "Ultra-fast Rotors for Molecular Machines and Functional Materials via Halogen Bonding: Crystals of 1,4-Bis(iodoethynyl)bicyclo[2.2.2]octane with Distinct Gigahertz Rotation at Two Sites"; Journal of the American Chemical Society, vol. 133; pp. 6371-6379; 2011.

Lenz, Robert W. et al.; Properties of a liquid crystalline polyester with a mesogen containing the bicyclooctylene ring: Liquid Crystals, 4:3; pp. 317-323; 1989.

Liu, Yanchun; "Synthesis and Characterization of Amorphous Cycloaliphatic Copolyesters with Novel Structures and Architectures"; Liu Dissertation submitted to Virginia Polytechnic Institute and State University; 260 pages; Mar. 22, 2012.

Liu, Yanchun and Turner, Richard; "Synthesis and Properties of Cyclic Diester Based Aliphatic Copolyesters"; Journal of Polymer Science: Part A: Polymer Chemistry, vol. 48; pp. 2162-2169; 2010.

Magro, Angel A. Núñez et al.; "The synthesis of amines by the homogeneous hydrogenation of secondary and primary amides"; Chemical Communications; pp. 3154-3156; 2007.

Nuding, G. et al; "Rodlike Molecules by Kolbe Electrolysis"; Synthesis; pp. 71-76; Jan. 1996.

Otera, Junzo; "Transesterification"; Chemical Reviews, vol. 93; pp. 1449-1470; 1993.

Polk, Malcolm et al.; "Thermotropic Copolyesters Containing the Bicyclo[2.2.2]Octane Ring System"; Molecular Crystals and Liquid Crystals Incorporating Nonlinear Optics, vol. 157; pp. 1-11; 1988.

Polk, Malcolm and Onwumere, Fidelis C.; "Thermotropic Copolyesters. 1. Synthesis and Characterization of Liquid Crystal Copolyesters Containing the Bicyclo[2.2.2]octane Ring System"; Journal Macromolecular Science-Chem., A23 (3); pp. 423-432; 1986.

Polk, Malcolm B. et al.; "Thermotropic Copolyesters. II. Synthesis and Characterization of Liquid-Crystal Copolyesters Containing the Bicyclo[2.2.2]Octane Ring System"; Journal of Polymer Science: Park A: Polymer Chemistry, vol. 24; pp. 1923-1931; 1986.

Polk, Malcolm B. et al.; "Thermotropic Copolyesters. III. Synthesis and Characterization of Liquid Crystal Copolyesters Containing the Bicyclo[2.2.2]octane Ring System"; Journal of Polymer Science: Park A: Polymer Chemistry, vol. 26; pp. 2405-2422; 1988.

Polshettiwar, Vivek et al.; "Silica-supported palladium: Sustainable catalysts for cross-coupling reactions"; Coordination Chemistry Reviews, vol. 253; pp. 2599-2626; 2009.

Roberts, John D. et al.; "Syntheses of Some 4-Substituted Bicyclo[2.2.2]octain-1-carboxylic Acids"; Journal of the American Chemical Society, vol. 75; pp. 637-640; Feb. 5, 1953.

Scheiner, Peter et al.; "Snthesis of Bicyclic Nitriles and Related Compounds. II"; Journal of Organic Chemistry, vol. 28; pp. 2960-2965; 1963.

Taimr, Ludek and Smith, James G.; "Polyesters Containing Bicyclo[2.2.2]octane and Bicyclo[3.2.2]nonane Rings"; Journal of Polymer Science: Part A-1, vol. 9; pp. 1203-1211; 1971.

Weis, Robert et al.; "4-Aminobicyclo[2.2.2]octanone Derivatives with Antiprotozoal Activities"; Monatshefte für Chemie (Chemical Monthly), vol. 134; pp. 1019-1026; 2003.

Whitney, Joel G. et al.; "Antiviral Agents. I. Bicyclo[2.2.2]octan- and -oct-2-enamines"; Journal Medical Chemistry, vol. 13; pp. 254-260; Mar. 1970.

Zhdankin, Viktor V.; "Hypervalent iodine(III) reagents in organic synthesis" APKIVOC—Special Issue Reviews and Accounts, (i); pp. 1-62; 2009.

Notification of Transmittal of the International Search Report and the Written Opinion of the International Searching Authority, or the Declaration dated Dec. 19, 2017 received in International Application No. PCT/US2017/056027.

Notification of Transmittal of the International Search Report and the Written Opinion of the International Searching Authority, or the Declaration dated Jan. 4, 2019 received in International Application No. PCT/US2018/055138.

Notification of Transmittal of the International Search Report and the Written Opinion of the International Searching Authority, or the Declaration dated Mar. 2, 2020 received in International Application No. PCT/US2019/065923.

Co-pending U.S. Appl. No. 16/339,950, filed Oct. 11, 2017; Yue Rachel Hu; now U.S. Pat. No. 10,633,315.

Co-pending U.S. Appl. No. 16/219,085, filed Dec. 13, 2018; David Scott Porter.

* cited by examiner

SYNTHESIS OF BICYCLO[2.2.2]OCTANE DERIVATIVES

CROSS-REFERENCE TO RELATED APPLICATION(S)

This application is a national stage filing under 35 USC § 371 of International Application Number PCT/US2018/055138, filed on Oct. 10, 2018, which claims the benefit of the filing date to U.S. Provisional Application No. 62/570,866, filed on Oct. 11, 2017, the entire disclosures of which are incorporated by reference herein.

FIELD OF THE INVENTION

This disclosure relates to the field of organic synthesis. In particular, it relates to a process for preparing a variety of 1,4-(substituted) bicyclo[2.2.2]octane derivatives.

BACKGROUND OF THE INVENTION

Bicyclo[2.2.2]octanes substituted at 1- and/or 4-positions are of great commercial interest. See, for example: (a) Joel G. Whitney, W. A. Gregory, J. C. Kauer, J. R. Roland, Jack A. Snyder, R. E. Benson and E. C. Hermann "Antiviral agents. I. Bicyclo[2.2.2]octan- and -oct-2-enamines" J. Med. Chem., 1970, 13, 254-60; (b) U.S. Pat. No. 3,546,290. (c) "4-Pyridyl and 4-(substituted-pyridyl) bicyclo[2.2.2]octane-1-amines" U.S. Pat. No. 3,367,941; and (d) Bicyclo [2.2.2] Acid GPR120 Modulators, US Pat. Appl. 2016/0039780.

Unfortunately, the bridgehead substituents of various bicyclic systems inclusive of the bicyclo[2.2.2]octane system are inert to nucleophilic substitution. Therefore, it would be useful to develop simple methods of preparation of the bridgehead bicyclo[2.2.2]octane derivatives. 1,4-Diacetoxybicyclo[2.2.2]octane is particularly interesting because it is a potential starting material for the preparation of various bridgehead bicyclo[2.2.2]octane derivatives. By way of example, U.S. Pat. No. 6,649,600 teaches various adenosine receptor antagonists, such compounds containing bridgehead bicyclo[2.2.2]octane substituents, which can be prepared from 1,4-diacetoxybicyclo[2.2.2]octane.

Bicyclo[2.2.2]octane derivatives also serve as important intermediates in the synthesis of natural products such as terpenes and alkaloids. (see, for example, Org. Biomol. Chem., 2006, 4, 2304-2312). They are also important building blocks for therapeutic agents for the treatment of metabolic syndrome (see, for example, Bioorg. Med. Chem. Lett., 2005, 15, 5266-5269) and other diseases (Org. Biomol. Chem., 2006, 4, 2304-2312).

Moreover, bicyclo[2.2.2]octane diols and diacids are useful as specialty monomers for certain polymers. See, for example, (a) G.B. 1,024,487; (b) J. Polym. Sci. Part A, 2010, Vol. 48, pp. 2162-2169; (c) U.S. Pat. No. 3,256,241, the contents and disclosure of which are hereby incorporated herein by reference; (d) U. S. Pat. No. 3,081,334, the contents and disclosure of which are hereby incorporated herein by reference; (e) Mol. Cryst. Liq. Cryst., 1981, Vol. 66, pp. 267-282; (f) J. Polym. Sci. A, 1994, Vol 32, pp. 2953-2960; and (g) J. Am. Chem. Soc. 1970, Vol 92, pp. 1582-1586.

Existing methods for the production of bicyclo[2.2.2] octane 1,4-substituted derivatives often involve expensive and toxic reagents, salt-forming reactions, costly reaction conditions, and suffer from poor net yields. (See, for example, Kopecký, Jan; Jaroslav, Šmejkal; and Vladimír, Hanuš; Synthesis of bridgehead bicyclo[2.2.2]octanols, Coll. Czech. Chem. Commun. 1981, 46, 1370-1375.) The reaction sequence is given in Scheme 1 below. Acid-catalyzed reaction of isopropenyl acetate with I,4-cyclohexanedione provides (besides 1,4-diacetoxy-I,4-cyclohexadiene) 1,4-diacetoxy-I,3-cyclohexadiene (I) which undergoes diene cycloaddition with maleic anhydride to provide 1,4-diacetoxybicyclo[2.2.2]oct-5-ene-2,3-dicarboxylic acid anhydride (II). Hydrogenation of (II) provides the saturated III which was hydrolyzed to the corresponding dicarboxylic acid (IV). Oxidative decarboxylation of (IV) with lead tetraacetate in pyridine in the presence of oxygen gave 1,4-diacetoxybicyclo[2.2.2]oct-2-ene (V) which upon hydrogenation gave diacetate (VI). The overall yield was reported to be 28-31%.

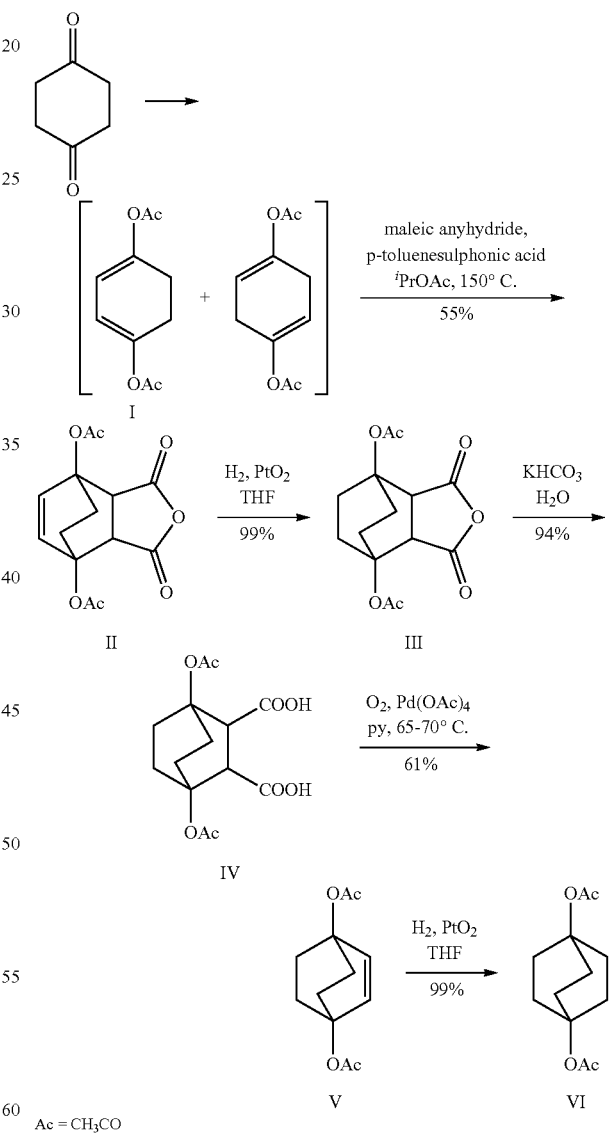

Scheme 1

Ac = CH₃CO

Beginning with 1,4-CHDM (1,4-cyclohexane dimethanol), a two-step conversion to 1,4-dimethylene cyclohexane is known (Scheme 2). (See J. Am. Chem. Soc., 1953, 75, 4780-4782.)

Scheme 2

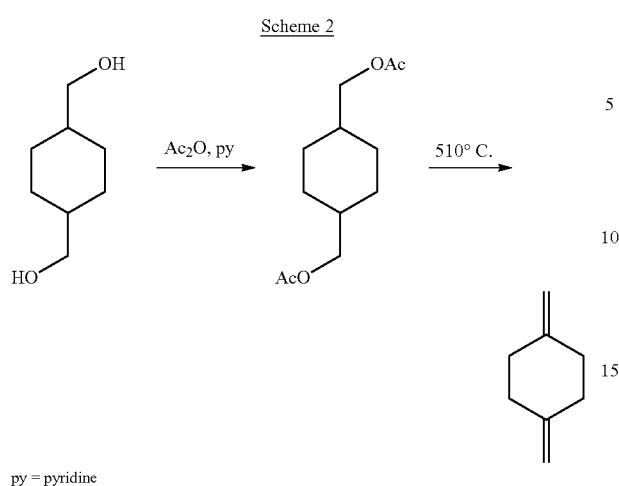

py = pyridine

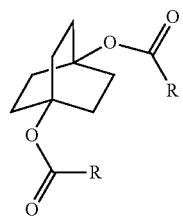

SUMMARY OF THE INVENTION

The disclosure is as set forth in the appended Claims. Briefly, this disclosure provides methodologies for derivatization of compounds of the formula

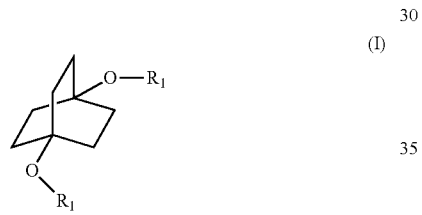
(I)

wherein each $R_1$ is independently hydrogen or a group of the formula

The compounds of Formula (I) can also be represented by the following formulae:

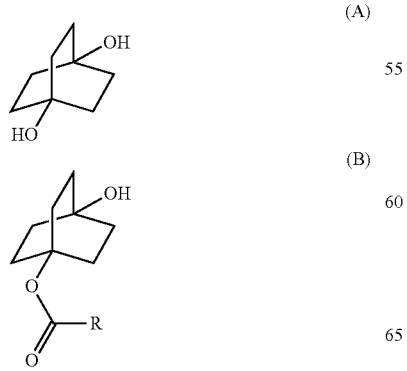
(A)
(B)

(C)

wherein R is as defined below.

The process of this disclosure thus represents a novel transition metal catalyzed chemical transformation. The method features the high conversion yield of 1,4-CHDM to 1,4-disubstituted bicyclo[2.2.2]octanes. The process of the disclosure thus affords a novel and simplified means for the commercial production of a wide variety of useful compounds having bridgehead bicyclo[2.2.2]octane substituents.

Aspect 1 of the present disclosure is a process comprising contacting a compound of the formula

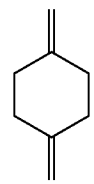

with (i) a transition metal catalyst comprising a palladium compound and (ii) an oxidizing agent;

optionally in the presence of at least one of
(I) a compound of the formula

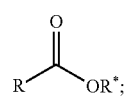

wherein R is chosen from hydrogen; and $C_1$-$C_{12}$ alkyl, optionally substituted by one or more of groups chosen from $C_1$-$C_6$ alkoxy, halo, nitro, and cyano;

and wherein R* is chosen from hydrogen; $C_1$-$C_{12}$ alkyl, optionally substituted by one or more of groups chosen from $C_1$-$C_6$ alkoxy, halo, nitro, and cyano; and an alkali metal cation; or (II) a compound having at least one $C_1$-$C_{12}$ alkanoyloxy moiety of the formula

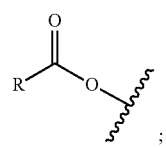

to afford a compound of the formula

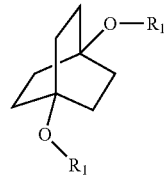
(I)

wherein each $R_1$ is independently hydrogen or a group of the formula

further comprising a step chosen from (a), (b), or (c):
(a) the step of reaction with carbon monoxide in the presence of a strong acid, followed by quenching with at least one of (i) water or (ii) an alcohol of the formula R—OH, to afford compounds of the formula

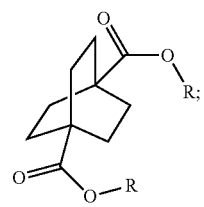

optionally further comprising the step of:

contacting with hydrogen in the presence of a heterogeneous copper catalyst or a homogeneous ruthenium catalyst to afford a compound of the formula

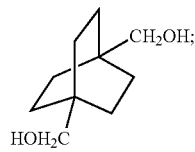

optionally followed by reductive amination to afford a compound of the formula

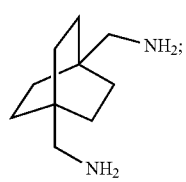

(b) the step of conversion to a compound of the formula:

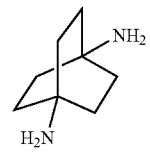

which comprises reaction of (I) with a nitrile in the presence of an acid followed by hydrolysis to the corresponding amine;
optionally further comprising treatment with phosgene ($COCl_2$) to afford a compound of the formula:

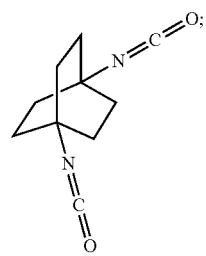 [SMILES: O=C=NC12CCC(N=C=O)(CC1)CC2]

or
(c) the step of halogenation of (I) to afford a compound of the formula:

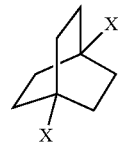

wherein x is halo;
optionally further comprising a step chosen from:
  a. reaction with carbon monoxide in the presence of a strong acid, followed by quenching with at least one of (i) water or (ii) an alcohol of the formula R—OH, to afford compounds of the formula

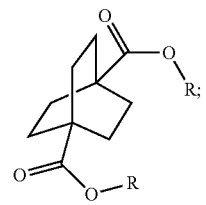

b. amination via treatment with ammonia to afford a compound of the formula:

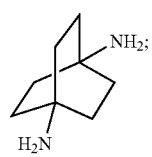

or c. hydroformylation via treatment with carbon monoxide and hydrogen in the presence of at least one of a cobalt or ruthenium catalyst at a temperature of about 90 to 250° C. and a pressure of about 5 to 300 bar, to afford a compound of the formula:

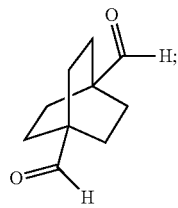

optionally further comprising:

a. treatment with an oxidizing agent, optionally in the presence of a homogeneous and/or heterogeneous catalyst to afford a compound of the formula:

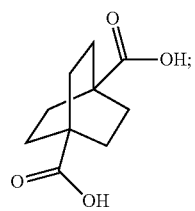 [SMILES: O=C(O)C12CCC(C(=O)O)(CC1)CC2]

or b. hydrogenation, optionally in the presence of a homogeneous and/or heterogeneous catalyst to afford a compound of the formula:

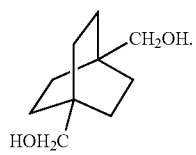

Aspect 2 is the process of aspect 1, represented by step (a).

Aspect 3 is the process of aspect 2, further comprising contacting with hydrogen in the presence of a hydrogenation catalyst to afford a compound of the formula

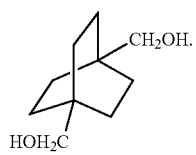

Aspect 4 is the process of Aspect 3, further comprising reductive amination to afford a compound of the formula

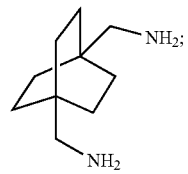

Aspect 5 is the process of aspect 2, further comprising one of the following steps:

(i) formation of an ammonium salt, followed by the application of heat;
(ii) formation of an acid halide, followed by treatment with ammonia; or
(iii) formation of an anhydride, followed by treatment with ammonia;

to afford a compound of the formula

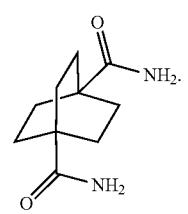 [SMILES: NC(=O)C12CCC(C(N)=O)(CC1)CC2]

Aspect 6 is the process of aspect 5, further comprising hydrogenation, optionally in the presence of a catalyst, to afford a compound of the formula

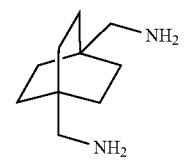

Aspect 7 is the process of aspect 1, represented by step (b).

Aspect 8 is the process of aspect 7, further comprising treatment with carbon monoxide and hydrogen in the presence of at least one of a cobalt or ruthenium catalyst at a temperature of about 90 to 250° C. and a pressure of about 5 to 300 bar; to afford a compound of the formula:

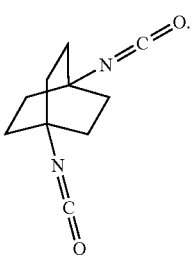 [SMILES: O=C=NC12CCC(N=C=O)(CC1)CC2]

Aspect 9 is the process of aspect 1, represented by step (c).

Aspect 10 is the process of aspect 9, further comprising reaction with carbon monoxide in the presence of a strong acid to afford a compound of the formula:

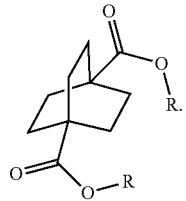

Aspect 11 is the process of aspect 9, further comprising amination via treatment with ammonia to afford a compound of the formula:

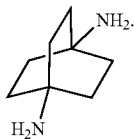

Aspect 12 is the process of aspect 9, further comprising hydroformylation via treatment with carbon monoxide and hydrogen in the presence of a ruthenium catalyst at a temperature of about 90 to 250° C. and a pressure of about 5 to 300 bar, to afford a compound of the formula:

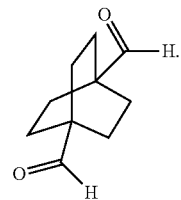

Aspect 13 is the process of aspect 12, further comprising treatment with an oxidizing agent to afford a compound of the formula:

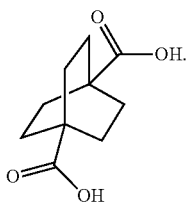 [SMILES: O=C(O)C12CCC(C(=O)O)(CC1)CC2]

Aspect 14 is the process of aspect 13, further comprising hydrogenation, optionally in the presence of a catalyst, to afford a compound of the formula:

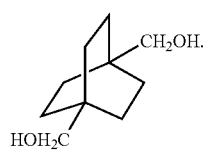

Aspect 15 of the present disclosure is a process for preparing a compound of the formula

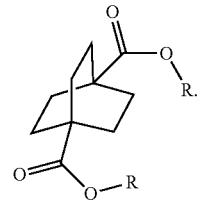

which comprises reaction of the compound of the formula

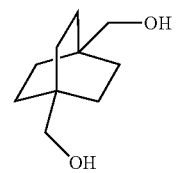

wherein each $R_1$ is independently hydrogen or a group of the formula

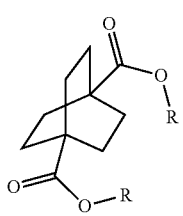

wherein R is independently hydrogen; $C_1$-$C_{12}$ alkyl, optionally substituted by one or more of groups chosen from $C_1$-$C_6$ alkoxy, halo, nitro, and cyano; or phenyl, optionally substituted by one or more of groups chosen from $C_1$-$C_6$ alkoxy, halo, nitro, cyano, and $C_1$-$C_{12}$ alkyl;

with carbon monoxide in the presence of a strong acid, followed by quenching with at least one of (i) water or (ii) an alcohol of the formula R—OH.

Aspect 16 of the present disclosure is a process for preparing a compound of the formula

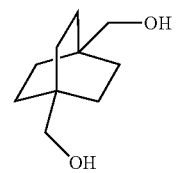

which comprises contacting a compound of the formula

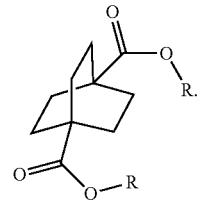

wherein R is $C_1$-$C_6$ alkyl, with hydrogen in the presence of a copper catalyst.

Aspect 17 of the present disclosure is a process for preparing a compound of the formula

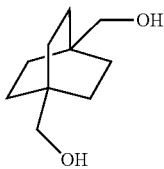 [SMILES: OCC12CCC(CO)(CC1)CC2]

which comprises contacting a compound of the formula

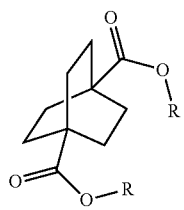

wherein R is $C_1$-$C_6$ alkyl, with hydrogen in the presence of a homogeneous ruthenium catalyst.

Aspect 18 of the present disclosure is a process for preparing a compound of the formula

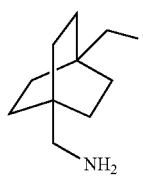 and/or 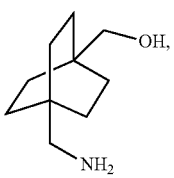

which comprises subjecting a compound of the formula:

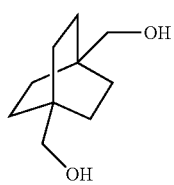 [SMILES: OCC12CCC(CO)(CC1)CC2]

to reductive amination.

Aspect 19 of the present disclosure are polymers which include monomers derived from compounds prepared by the processes of aspect 1-18 of this disclosure.

DETAILED DESCRIPTION OF THE INVENTION

The disclosure provides a process comprising contacting a compound of the formula

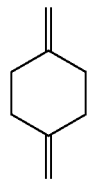

with (i) a transition metal catalyst comprising a palladium compound and (ii) an oxidizing agent;
optionally in the presence of at least one of
(I) a compound of the formula

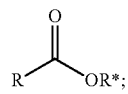

wherein R is chosen from hydrogen; and $C_1$-$C_{12}$ alkyl, optionally substituted by one or more of groups chosen from $C_1$-$C_6$ alkoxy, halo, nitro, and cyano;
and wherein R* is chosen from hydrogen; $C_1$-$C_{12}$ alkyl, optionally substituted by one or more of groups chosen from $C_1$-$C_6$ alkoxy, halo, nitro, and cyano; and an alkali metal cation; or
(II) a compound having at least one $C_1$-$C_{12}$ alkanoyloxy moiety of the formula

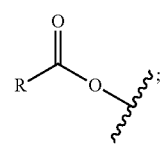

to afford a compound of the formula

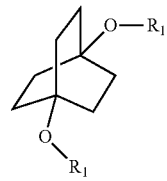 (I)

wherein each $R_1$ is independently hydrogen or a group of the formula

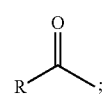

further comprising a step chosen from (a), (b), or (c):
(a) the step of reaction with carbon monoxide in the presence of a strong acid, followed by quenching with at least one of (i) water or (ii) an alcohol of the formula R—OH, to afford compounds of the formula

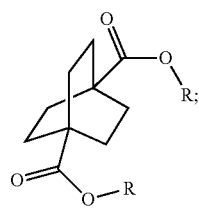

optionally further comprising the step of:
contacting with hydrogen in the presence of a heterogeneous copper catalyst or a homogeneous ruthenium catalyst to afford a compound of the formula

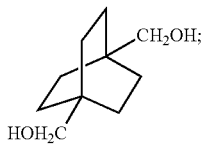

optionally followed by reductive amination to afford a compound of the formula

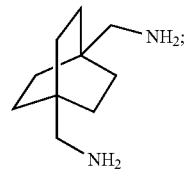

(b) the step of conversion to a compound of the formula:

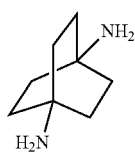

which comprises reaction of (I) with a nitrile in the presence of an acid followed by hydrolysis to the corresponding amine (XVI, XVII);
optionally further comprising treatment with phosgene (COCl$_2$) to afford a compound of the formula:

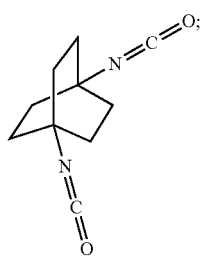 [SMILES: O=C=NC12CCC(N=C=O)(CC1)CC2]

or
(c) the step of halogenation of (I) to afford a compound of the formula:

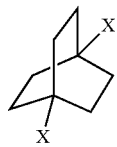

wherein x is halo;
optionally further comprising a step chosen from:
a.) reaction with carbon monoxide in the presence of a strong acid, followed by quenching with at least one of (i) water or
(ii) an alcohol of the formula R—OH, to afford compounds of the formula

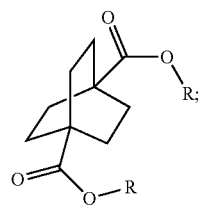

b.) amination via treatment with ammonia to afford a compound of the formula:

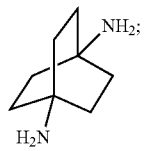

and
c.) hydroformylation via treatment with carbon monoxide and hydrogen in the presence of at least one of a cobalt or ruthenium catalyst at a temperature of about 90 to 250° C. and a pressure of about 5 to 300 bar, to afford a compound of the formula:

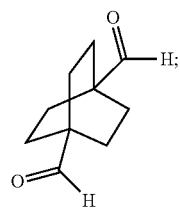

optionally further comprising:
a. treatment with an oxidizing agent to afford a compound of the formula:

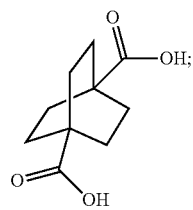 [SMILES: O=C(O)C12CCC(C(=O)O)(CC1)CC2]

or b. hydrogenation, to afford a compound of the formula:

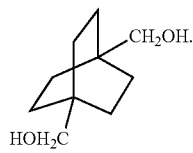

Further details regarding the synthesis of compounds of Formula (I) can be found in PCT Application No. PCT/US17/56027 filed on this date, incorporated herein by reference. In this disclosure, starting with certain compounds of Formula (I) above, various 1,4-derivatives of the bicyclo[2.2.2]octane structure can be prepared. In certain embodiments, the disclosure provides processes for preparing 1,4-bicyclo[2.2.2]octane compounds having bridgehead functional groups selected from dimethanol;
diamine;
diacid;
diester;
dialdehyde,
dihalide,
diisocyanate and
diamido groups Such subsequent chemical transformations can be illustrated in the flow diagram below:

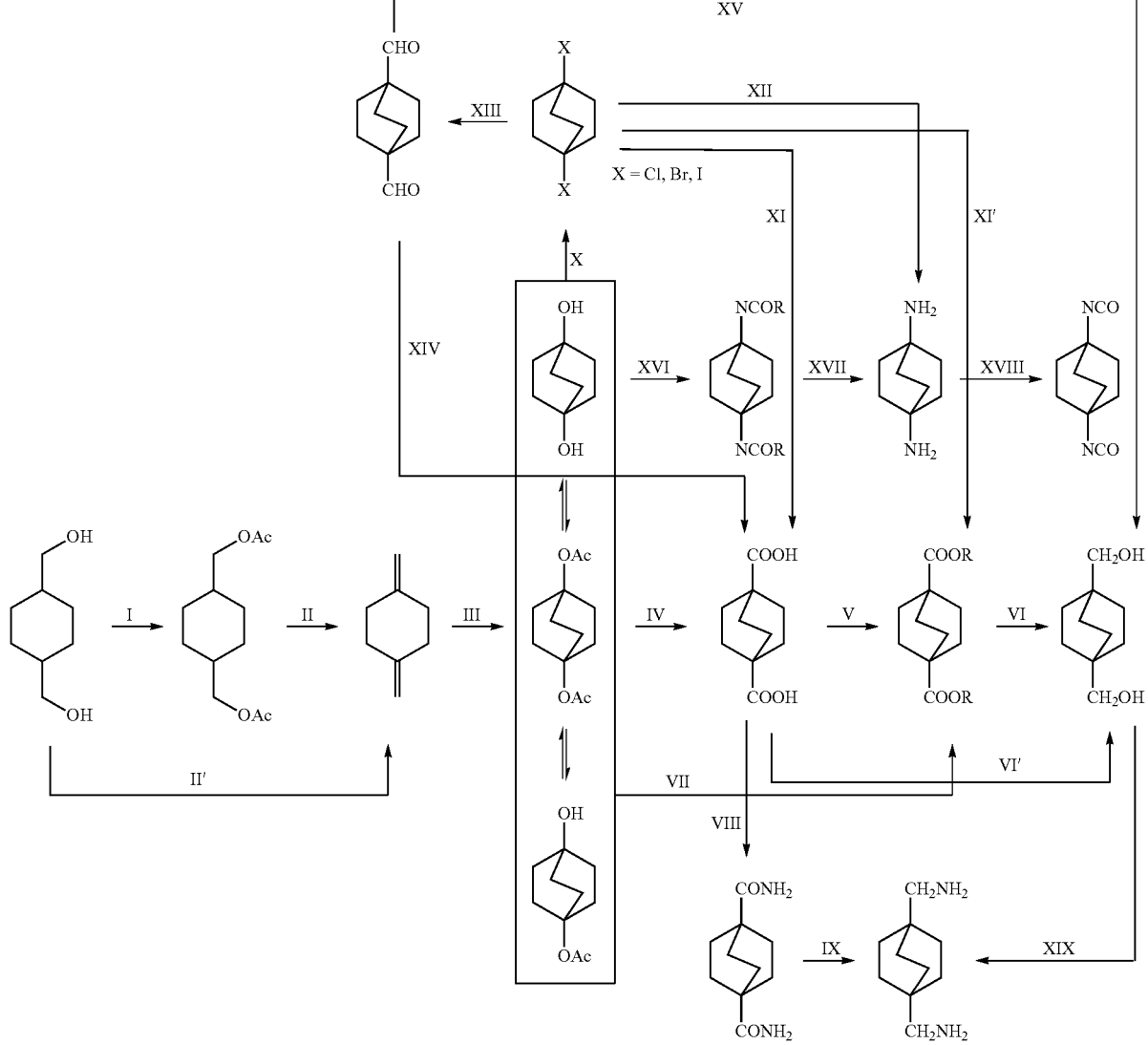

In one embodiment, the disclosure provides a process for preparing a compound of the formula

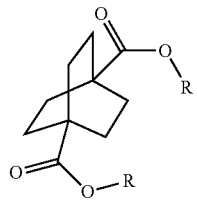

which comprises reaction of the compound of the formula

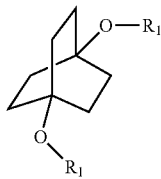

wherein each $R_1$ is independently hydrogen or a group of the formula

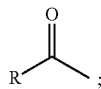

wherein R is independently hydrogen; $C_1$-$C_{12}$ alkyl, optionally substituted by one or more of groups chosen from $C_1$-$C_6$ alkoxy, halo, nitro, and cyano; or phenyl, optionally substituted by one or more of groups chosen from $C_1$-$C_6$ alkoxy, halo, nitro, cyano, and $C_1$-$C_{12}$ alkyl;

with carbon monoxide in the presence of a strong acid, followed by quenching with at least one of (i) water or (ii) an alcohol of the formula R—OH.

In the above embodiment, referring to steps IV and VII in the scheme above, the compounds of Formula I are reacted with carbon monoxide in the presence of a strong acid such as sulfuric acid, anhydrous HF, $BF_3$, triflic acid, $SbF_5$/HF, $SbF_5$/$SO_2$ClF, $SbF_5$/$SO_2$, $SbF_5$/$HSO_3$F and the like. For the cyclic compound 1,4-diacetoxybicyclo[2.2.2]octane, concentrated phosphoric acid and trifluroacetic acid do not work in the current process. If sulfuric acid is used, it is necessary to use the concentrated form, i.e. in a concentration above 90% and in another embodiment above 96%. The concentration chosen is dependent on the reaction temperature and pressure. In general, higher concentration is required under milder conditions. Dilute sulfuric acid generally leads to the obtaining of reaction mixtures containing relatively little if any of the desired products. In certain embodiments of this process, 107% fuming sulfuric acid was used for reactions conducted at room temperature. Mole ratios of sulfuric acid to bicyclic compound charge is in the range of from about 2:1 to about 100:1. Greater or lesser amounts of sulfuric acid may, however, be employed within the scope of the disclosure.

Catalysts may be used within the scope of this aspect of the disclosure to lower the reaction temperature and pressure, but is not necessary. If used, potential catalysts include transition metal complexes from Group VIIIB and IB (CAS) that can form carbonyl cations under the current reaction conditions. Examples include Cu, Au, Pd, Ir, Ni, etc.

The carbon monoxide reactant need not necessarily be pure. Suitable carbon monoxide charge materials comprise the commercially available carbon monoxide and carbon monoxide-containing gases. The presence therein of fixed gases and minor amounts of saturated hydrocarbons does not adversely affect the efficiency of the process.

Solvents which are liquid under the conditions of execution of the reaction may be used within the scope of the disclosure to facilitate the dissolving of the bicyclic compound, but are not necessary. Such solvent comprises, for example, normally liquid saturated hydrocarbons, such as pentane, hexane, heptanes, octanes; carboxylic acids, such as heptanoic acid; aliphatic ketones, such as dimethyl ketone; etc. The solvent employed may be added to the organic charge or introduced separately into the reaction zone.

The reaction of the bicyclic compound with carbon monoxide is carried out at relatively mild conditions. Temperatures utilized are, for example, from about −10° to about 100° C., or in the range of from about 20° to about 60° C. Pressures ranging from about atmospheric to about 4000 p.s.i.g and higher may be used. Pressures in the range of, for example, from about 100 to about 2000 p.s.i.g. can also be utilized. While conducting such reactions, it is desired that one avoid the introduction of substantial amounts of water into the reaction zone from an outside source during the course of the reaction of the organic charge with the carbon monoxide.

The bicyclic compound as well as the carbon monoxide charge to the process, may be subjected to suitable pretreatment to effect the removal of water and/or impurities therefrom. Such pretreatment may comprise one or more such steps as, for example, distillation, contact with suitable adsorbent material such as, for example, charcoal, adsorptive alumina, clays, etc.; the step chosen being governed by the material treated and the amount of impurity or water to be removed. Fuming sulfuric acid may be used in the process to remove the water residue from starting materials (bicyclic compound and carbon monoxide).

The reaction of the bicyclic compound with carbon monoxide in the presence of concentrated strong acid may be executed in batch, continuous, or semi-continuous operations.

Upon completion of the reaction of the carbon monoxide with the bicyclic compound, flow of carbon monoxide to the reaction mixture is stopped, and if the mixture is at a temperature substantially above room temperature it is cooled to a temperature not substantially in excess of about 20° C. and brought to about atmospheric pressure.

The reaction mixture obtained is thereupon diluted with quenching reagent selected from water, alcohols, amines or their mixtures. The amount of quenching reagent thus added to the reaction mixture may vary considerably within the scope of the disclosure. The quenching reagent may be added to the reaction mixture in an amount ranging, for example, from as little as about 3% to as much as about 2,000% by volume of the acid originally charged is found satisfactory. Greater or lesser amounts of water may, however, be employed within the scope of the disclosure. In a preferred method of carrying out the disclosure the quenching reagent is added to the reaction mixture in an amount equal to from about 75% to about 500% by volume of the acid originally charged. Dilution of the reaction mixture is preferably carried out without substantial increase in temperature. It will be noted that the addition of water to the reaction mixture is effected only after completion of the reaction of carbon monoxide with bicyclic compound. The water addition is effected in the absence of carbon monoxide addition and preferably in the absence of a free carbon monoxide atmosphere. The addition of the water is preferably effected at temperatures and pressures which do not substantially exceed, and which may be less than atmospheric.

In the examples below, water was used as quenching reagent. The resulting bicyclo[2.2.2]octane 1,4-dicarboxylic acid precipitated out of the solution as white solid. Pure bicyclo[2.2.2]octane 1,4-dicarboxylic acid was obtained by recrystallization from basic/acidic aqueous solution.

The diester can also be derived from diacid by reacting with an alcohol in the presence of an esterification catalyst such as HCL, $H_2SO_4$, solid acids, transition metal catalysts such as Sn, Ti complexes, etc. (step V). See, for example, Tin-Catalyzed Esterification and Transesterification Reactions: A Review, Arthur Batista Ferreira, Abiney Lemos Cardoso, and Márcio José da Silva, ISRN Renewable Energy, Volume 2012 (2012), Article ID 142857, 13 pages, doi:10.5402/2012/142857; Transesterification, Junzo Otera, Chem. Rev. 1993, 93. 1449-1470. In the alternative, the diacid may be reacted with an alcohol at elevated temperatures, for example, from 100° to 300° C. in the absence of an acid catalyst. After either reaction, the crude diester thus produced may be purified by sublimation, crystallization or column chromatography.

In a further embodiment, this disclosure provides a process for preparing a compound of the formula

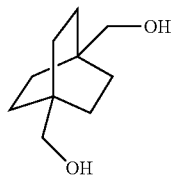 [SMILES: OCC12CCC(CO)(CC1)CC2]

which comprises contacting a compound of the formula

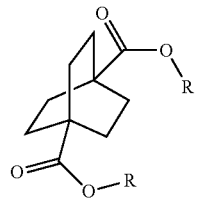

wherein R is $C_1$-$C_6$ alkyl, with hydrogen in the presence of a copper catalyst. (Steps VI and VI')

In one embodiment, when the diester is used in the process, a wide variety of copper-based catalysts may be used in this aspect of the disclosure. Examples include but are not limited to:

1) Copper catalysts containing single component, such as Raney copper and monometallic copper catalyst deposited on a catalyst support material such as carbon, silica, fiber, etc.
2) Copper catalysts containing binary components, such as copper catalysts supported on different metal oxides. Examples of metal oxides include but not limited to $Cr_2O_3$, $Al_2O_3$, ZnO, ZrO, $TiO_2$, MgO etc.
3) Copper catalysts containing tertiary or more components, such as copper chromite which contains promoters such as barium, manganese, etc. Other copper-based catalysts containing another co-catalyst also fall into this catalog, such as copper oxide/zinc oxide deposited on a catalyst support material such as alumina, magnesium oxide and titania.

It is only necessary that the catalyst be reasonably active, and that its activity for catalyzing formation of by-products be relatively much lower than its activity for catalyzing the hydrogenolysis (hydrogenation) reaction.

In one embodiment, the catalysts comprise, in their reduced/active form, about 25 to 60 weight percent copper and about 10 to 35 weight percent chromium, manganese or a combination thereof. Suitable copper oxide/zinc oxide catalyst precursors include CuO/ZnO mixtures wherein the Cu:Zn weight ratio ranges from about 0.4:1 to about 2:1 which are promoted with from about 0.1% by weight up to about 15% by weight manganese. Suitable copper chromite catalyst precursors include those wherein the Cu:Cr weight ratio ranges from about 0.1 to about 4:1, or from about 0.5:1 to about 4:1. Promoted copper chromite precursors include copper chromite catalyst precursors wherein the Cu:Cr weight ratio ranges from about 0.1:1 to about 4:1, or from about 0.5:1 to about 4:1, which are promoted with from about 0.1% by weight up to about 15% by weight manganese. Manganese-promoted copper catalyst precursors typically have a Cu:Mn weight ratio of from about 2:1 to about 10:1 and can include an alumina support, in which case the Cu:Al weight ratio typically is from about 2:1 to about 4:1.

The physical form of the catalyst is not critical and normally is determined by the mode in which the process is operated. For example, pellets having an average diameter of 1 to 6 mm and a length of 2 to 12 mm may be employed in the process wherein the reactant is passed over and through one or more fixed beds of catalyst in a mode of operation referred to as trickle bed operation. The reaction may be run either continuously, semi-continuous or batch-wise using, for example, a copper catalyst in the form of a powder. Operation of the process in the vapor phase is also within the scope of this disclosure.

The hydrogenolysis conditions of temperature and pressure are, in general, important but can be varied over a wide range. Normally, the process will be operated at temperatures in the range of about 120 to 350° C. As would be expected, lower temperatures result in lower reaction rates, while temperatures which are excessively high increase the amount of undesirable by-products. In one embodiment, temperature range is between 200 and 260° C. These temperatures refer to the mean temperature of the catalyst bed, when the reaction is conducted in a continuous trickle-bed reactor. The pressure may be varied between about 1000 psig and 6000 psig. In one embodiment, pressure is between 2000 psig and 4000 psig. Lower pressures generally lead to lower conversion, while higher pressures increase both the energy and equipment cost of the operation.

The reaction can be carried out in the neat condition or in the presence of glycol or mono-alcohol or mixtures as solvent. Examples of suitable glycol include ethylene glycol, propane diol, CHDM, etc. Hydrogenolysis product bicyclo [2.2.2]octane-1,4-dimethanol can also be used as solvent. Examples of suitable mono-alcohol include methanol, ethanol, n-propanol, n-butanol, etc., or mixtures thereof.

In another embodiment, when the diester or the diacid is used, a wide variety of conventional homogeneous hydrogenation catalysts that are effective for the reduction of carboxylic/carboxylate groups to a hydroxymethyl group may also be used in the process of this disclosure (See, for example U.S. Pat. No. 9,328,050 incorporated herein by reference. The catalyst can be a homogeneous catalyst that is dissolved or dispersed in the solvent. In certain embodiments of the process, the catalyst comprises: a) a ruthenium, rhodium, iron, osmium or palladium compound; and (b) an organic compound as ligand. In certain embodiments, the catalyst of the present disclosure is a ruthenium compound. The ruthenium compound is not particularly limiting and can be any ruthenium source that is soluble in the solvent of this disclosure. Exemplary compounds include ruthenium salts, hydride complexes, carbonyl compounds, halides, oxides, phosphine complexes, and combinations of two or more of the foregoing. In certain embodiments, the ruthenium compounds can be converted to active species under the reaction conditions. In certain embodiments, the organic compound is a tridentate ligand. Selected tridentate compounds include but not limited to 1,1,1-tri(diarylphosphinomethyl)alkyl in which the alkyl is substituted or unsubstituted, 6-(di-t-butylphosphinomethyl)-2-(N,N-diethylaminomethyl)pyridine (in Milstein catalyst), bis[2-(diphenylphosphino)ethyl]amine (in Ru-MACHO), and other pincer ligands. Further, in certain embodiments of the process the ruthenium compound and the tridentate compound are the same compound. For example, in one embodiment, the catalyst is Milstein catalyst (diester); in another embodiment, the catalyst is Ru-MACHO® catalyst (diester), available from Sigma-Aldrich. In another embodiment, the catalyst is Ru(TriPhos) (diacid).

In certain embodiments, the process further comprises feeding to the second reaction zone a promotor. In Ru-1,1,1-tri(diarylphosphinomethyl)alkyl system, the promotor is selected from Lewis acids, protonic acids having an ionization constant (Ki) of $5 \times 10^{-3}$ or greater, onium salts, and combinations of two or more of the foregoing. In certain embodiments, the promotor is selected from ammonium hexafluorophosphate, tetrabutylammonium hexafluorophosphate, tetraphenylphosphonium bromide, sodium tetraphenyl borate, ammonium tetrafluoroborate, tetramethyl ammonium tetrafluoroborate, toluenesulfonic acid, phosphoric acid, triflic acid, sulfuric acid, methanesulfonic acid, trifluoroacetic acid, dodecylbenzenesulfonic acid, dinonylnaphthalenesulfonic acid, and combinations of two or more of the foregoing. In certain embodiments, the promotor is selected from tetrabutylammonium hexafluorophosphate, toluenesulfonic acid, triflic acid, dodecylbenzenesulfonic acid, dinonylnaphthalenesulfonic acid, and combinations of two or more of the foregoing. (See for example, U.S. Pat. No. 9,328,050, incorporated herein by reference.)

If the precursor of Ru-MACHO or Milstein catalyst is used, the promotor is added to remove the chloride ligand to generate the active catalyst species. Selected promotors include potassium salts, sodium salts and silver salts (these salts form insoluble chloride salts) with non or weak coordinating anions. Selected promotors include but not limited to potassium hydroxide, potassium methoxide, sodium hydroxide, sodium methoxide.

The hydrogenolysis conditions of temperature and pressure are, in general, critical and can be varied over a wide range depending on the nature of the catalyst selected. Normally, the process will be operated at temperatures in the range of about 100 to 250° C. As would be expected, lower temperatures result in lower reaction rates, while temperatures which are excessively high increase the amount of undesirable by-products or catalyst deactivation. In some embodiments (Milstein catalyst and Ru-MACHO), the preferred temperature range is between 100 and 160° C. In some embodiments (Ru-triphos), the preferred temperature range is between 160 and 250° C. The hydrogen pressure may be varied between about 100 psig and 3000 psig. Lower pressures generally lead to lower conversion, while higher pressures increase both the energy and equipment cost of the operation.

A wide range of solvents may be used in the process of this disclosure. The solvent needs to be liquid phase and dissolve or partly dissolve the starting material, catalyst and promotor under the process condition. Examples of suitable solvents include alcohols, hydrocarbons, water, ethers, amines, amides, etc. In the embodiments, p-xylene was selected as solvent.

The reaction may be run either continuously, semi-continuous or batchwise. See U.S. Pat. No. 9,328,050.

In a further embodiment, this disclosure provides a process for preparing a compound of the formula

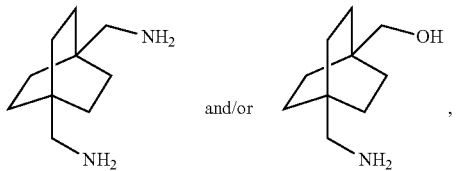 [SMILES: NCC12CCC(CN)(CC1)CC2 ; NCC12CCC(CO)(CC1)CC2]

and/or which comprises subjecting a compound of the formula:

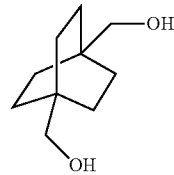 [SMILES: OCC12CCC(CO)(CC1)CC2]

to reductive amination.

In the experiments below, Raney Ni is used as catalyst. Other catalysts could also be used.

In another embodiment, referring to step VIII in the reaction scheme above, the dicarboxylic acid may be converted to the corresponding amide via known methods. There are three possible routes: 1) the dicarboxylic acid may be first converted to an ammonium salt, which then affords the corresponding amide upon heating. The ammonium salt may be formed by adding an ammonium salt, for example, ammonium carbonate to an excess in order to drive the equilibrium to the desired ammonium salt, which then dehydrates upon application of heat to form the amide; 2) the dicarboxylic acid may be converted to the corresponding acid chloride which can then be treated with a concentrated solution of ammonia in water to form the amide; 3) the dicarboxylic acid may be converted to an anhydride which can then be treated with ammonia to form amide. (See, for example, www.chemguide.co.uk/organicprops/amides/preparation.html).

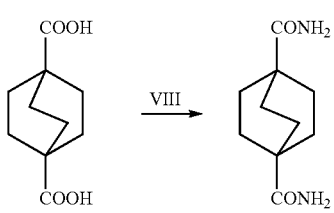

In another embodiment, referring to step IX in the scheme above, the diamide may be transformed to the corresponding amine by hydrogenation.

Process 1: Non-catalytic route with reducing agents such as lithium aluminum hydride, lithium borohydride in mixed solvents of tetrahydrofuran and methanol.

Process 2: Heterogeneous catalysis: 1) Cu—Cr oxide catalysts at high $H_2$ pressure (~300 bar) and reaction temperature (250° C.) (JACS 1934, 56, 247). Additives such as $NH_3$ or 4A zeolite could improve the selectivity or reaction conditions (Helv. Chim. Acta 1955, 38, 1649-1654; U.S. Pat. No. 4,448,998). 2) The bimetallic catalysts consisting of group 8 to 10, and group 6 or 7 metals (e.g. Rh/Re, Rh/Mo, Ru/Re, Ru/Mo) show extremely potent reducing abilities in the hydrogenation of amides (100 atm of H2 at 160° C.) (TL 1996, 37, 6749-6752).

Process 3: Homogeneous catalysis: $Ru(acac)_3$/triphos (Chem. Commun. 2007, 3154-3156) (Milstein's catalyst cleaves C—N bond).

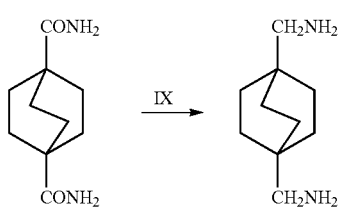

In a further embodiment, referring to step X in the scheme above, the compounds of Formula I above may be converted to the corresponding dihalide via known methodology. See for example, (Collection Czechoslov. Chem. Cornrnun. 1979, 2965). For example, one can react compounds of Formula I with halogenation agents, such as alkali halogenide (NaCl, KBr, KI) and inorganic acid halides ($SOCl_2$, $POCl_3$, $PBr_3$), and strong acids (e.g. 100% $H_3PO_4$, polyphosphoric acid, sulfuric acid) at temperatures 80-150° C. After cooling, the mixture can be quenched with ice water and extracted with organic solvent (e.g. ether, chloroform, ethyl acetate). The organic layer can be washed with $NaHCO_3$ aqueous solution, water, brine and dried with $MgSO_4$. After solvent evaporation, the crude dihalide can be purified by sublimation, crystallization or column chromatography.

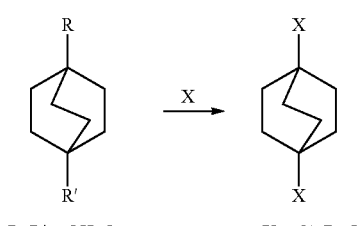

In a further embodiment, referring to steps XI and XI' in the above scheme, the dihalide compounds may be converted to the corresponding diester under conventional Koch Reaction conditions.

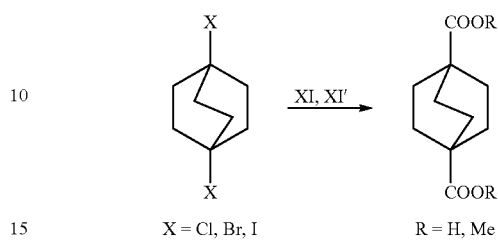

In a further embodiment, referring to step XII in the scheme above, the dihalide compound may be transformed to the corresponding diamine by, for example, heating the dihalide with ammonia in ethanol. The reaction may be carried out in a sealed tube. See http://www.chemguide.co.uk/organicprops/amines/preparation.html)

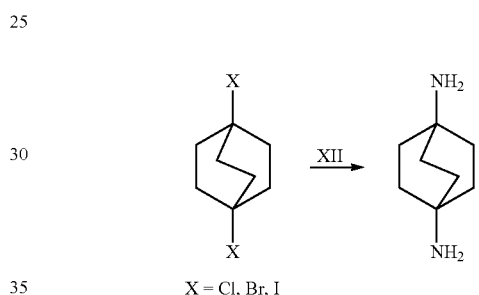

In a further embodiment, referring to step XIII in the scheme above, the dihalide compound may be converted to the corresponding dialdehyde via a conventional hydroformylation step. For example, this may be accomplished by reacting dihalide with carbon monoxide and hydrogen in the presence of [Co] or [Rh] catalyst, at a temperature of about 90-250° C., and a pressure of about 5-300 bar.

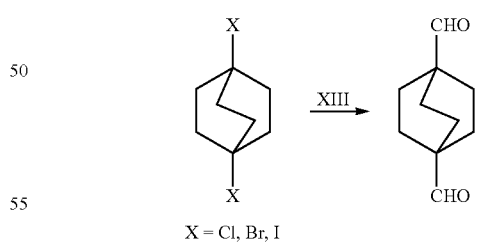

In a further embodiment, the dialdehyde may be converted to the corresponding diacid via oxidation by the following processes.

Process 1: Non-catalytic route: reacting aldehyde with oxidants such as chromic acid, chromate salts, dichromate salts, permanganate, etc. under acidic condition.

Process 2: Co/Mn/Br catalyzed oxidation with $O_2$ in acetic acid (milder TPA process).

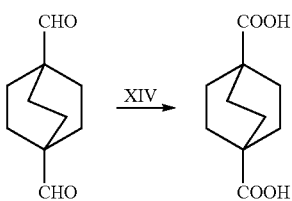

In a further embodiment, the referring to step XV in the scheme above, the dialdehyde may be converted to the corresponding dimethanol compound via hydrogenation through the following processes.

Process 1: Non-catalytic route: reduction with stoichiometric amount of reducing agents such as LiAlH4 and NaBH4.

Process 2: Heterogeneous hydrogenation

Process 3: Homogeneous hydrogenation

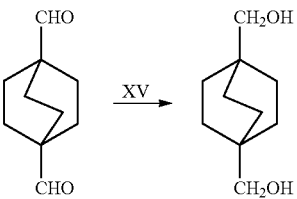

In a further embodiment, referring to step XVI in the above scheme, compounds of Formula I (without purification) can be converted to the corresponding dialkylamides via a Ritter reaction. For example, the compounds of Formula I may be reacted with a nitrile in the presence of a strong acid. The resulting nitrilium ion is then hydrolyzed by water to the desired dialkylamide

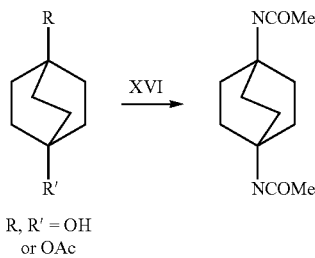

R, R' = OH or OAc

In another embodiment, referring to step XVII in the above scheme, the dialkylamides can be converted to the corresponding diamines via acid (e.g., HCL) or base-catalyzed (e.g., KOH) hydrolysis using known methodology.

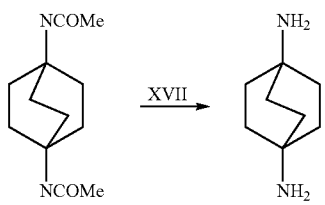

In another embodiment, referring to step XVIII in the above scheme, the diamine compounds may be converted to the corresponding isocyanates by treatment with phosgene ($COCl_2$).

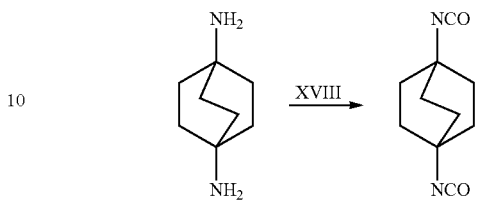

The present disclosure includes and expressly contemplates any and all combinations of aspects, embodiments, features, characteristics, parameters, and/or ranges disclosed herein. That is, this disclosure may be defined by any combination of aspects, embodiments, features, characteristics, parameters, and/or ranges mentioned herein. As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations (even when not qualified by the term "about"). These values and ranges may vary from their stated numbers depending upon the desired properties sought to be obtained by the present disclosure as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within
the range including sub-ranges such as 60 to 90 and 70 to 80.

The content of all documents cited herein, including patents as well as nonpatent literature, is hereby incorporated by reference in their entirety. To the extent that any incorporated subject matter contradicts with any disclosure herein, the disclosure herein shall take precedence over the incorporated content.

This disclosure can be further illustrated by the following examples of certain embodiments thereof, although it will be understood that these examples are included merely for purposes of illustration and are not intended to limit the scope of this disclosure unless otherwise specifically indicated.

EXAMPLES

Preparation of a Mixture of 4-ACETOXYBICYCLO[2.2.2]OCTAN-1-OL, 1,4-DIACETOXYBICYCLO[2.2.2]OCTANE AND BICYCLO[2.2.2]OCTANE-1,4-DIOL from 1,4-CYCLOHEXANEDIMETHANOL (CHDM)

1,4-Dimethylene cyclohexane was prepared by following the literature procedure with small modifications. (William J. Bailey, Harold R. Golden, Cyclic Dienes. I. 1,2-Dimethylenecyclohexane, J. Am. Chem. Soc., 1953, 75, 4780-4782). 1,4-Cyclohexanedimethanol (CHDM) (3250 g, 22.5 mol) and pyridine (5.5 g, 0.07 mol) were heated to 125° C. in a 20-liter reactor fitted with dropping funnel and reflux condenser. Over a period of 2 hours, acetic anhydride (7020 g, 68.8 mol) was added to the glycol. After the addition, the mixture was stirred for 1.5 hours at 125° C. After acetic acid and anhydride were removed by vacuum distillation, CHDM diacetate (5100 g, 99% yield) was collected. The reaction was also successfully performed using DMAP and Nafion as catalyst.

At a rate of 0.5 g per minute, 2000 g (8.8 mol) of CHDM diacetate was dropped into a 1-in. quartz column heated to 540° C. by a Lindberg/Blue M furnace (Model number: HTF55347C) and paced to a depth of 27 in. with 0.25-in. quartz chips. The addition was conducted in nitrogen atmosphere by introducing a slow stream of nitrogen (25 ccm) at the top of the column. The pyrolysate was collected in a 3-liter flask cooled in an ice bath. GC-MS of the pyrolysate shows mainly 1,4-dimethylene cyclohexane and acetic acid with trace amount of unreacted CHDM diacetate and (4-methylenecyclohexyl)methyl acetate. Distillation of the pyrolysate gives azeotrope that contains 1, 4-dimethylene cyclohexane and acetic acid with a mole ratio of 1:2. Pure 1,4-dimethylene cyclohexane can be obtained by washing the azeotrope with distilled water.

1,4-Dimethylene cyclohexane (10 g, 93 mmol), palladium diacetate (200 mg, 0.9 mmol), and acetic acid (50 g), were charged to a 250 mL round bottom flask equipped with a ¾ inch magnetic stir bar. To the resulting mixture, which was cooled with ice bath, 30% of hydrogen peroxide aqueous solution (15 g) was added dropwise under rapid stirring. The resulting yellow solution was stirred at room temperature for overnight and analyzed by GC-MS, showing the formation of 4-acetoxybicyclo[2.2.2]octan-1-ol, 1,4-diacetoxybicyclo[2.2.2]octane and bicyclo[2.2.2]octane-1,4-diol. The conversion of 1,4-Dimethylene cyclohexane was 59.7%. The selectivities of 4-acetoxybicyclo[2.2.2]octan-1-ol, 1,4-diacetoxybicyclo[2.2.2]octane and bicyclo[2.2.2]octane-1,4-diol were 52.6%, 22.4%, 19.3%.

1,4-Dimethylene cyclohexane (5 g, 0.046 mol) and palladium dichloride (0.248 g, 0.0014 mol, 3 mol %) were added to a 125 mL flask. To the flask was added 25% oxone aqueous solution (28.27 g, 0.092 mol, 2 eq) dropwise over ca. 2 hours. The reaction was exothermic. The reaction mixture was stirred overnight. Analysis by GCMS showed conversion to bicyclo[2.2.2]octane-1,4-diol. The reaction mixture was filtered to remove undissolved PdCl2. The aqueous solution was extracted 4× with n-butanol. The organic extracts were combined, dried over MgSO4 and concentrated in vacuo to afford a dark residue. Analysis by GCMS confirmed that bicyclo[2.2.2]octane-1,4-diol was present with trace n-butanol.

1,4-Diacetoxybicyclo[2.2.2]octane was also prepared according to literature procedure. (See Kopecký, Jan; Jaroslav, Šmejkal; and Vladimír, Hanuš; Synthesis of bridgehead bicyclo[2.2.2]octanols, *Collection of Czechoslovak Chemical Communications* 1981, 46, 1370-1375.)

Example 1

20 cc of fuming sulfuric acid (prepared from 10 cc 96% sulfuric acid and 10 cc 20% fuming sulfuric acid) and 1 g of 1,4-diacetoxybicyclo[2.2.2]octane were charged to a 100 mL stainless steel autoclave reactor equipped with glass liner and stirrer. The assembled autoclave reactor was pressurized with carbon monoxide to 2000 psig pressure. The reactor was maintained at a stirring rate of 600 rpm, a temperature of 23° C. and a pressure of 2000 psig for 16 hours. At the end of this period the pressure was reduced to atmospheric by cutting off the source of carbon monoxide and venting. The reaction mixture was then diluted with 100 cc water; care being taken to maintain the temperature below about 30° C. throughout the dilution. Dilution of the reaction mixture resulted in the formation of white precipitates, which were collected via filtration. The precipitates were dissolved in saturated $NaHCO_3$ aqueous solution and re-precipitated via acidification of the solution by concentrated HCl. The precipitates, which are pure bicyclo[2.2.2]octane 1,4-dicarboxylic acid, were collected (524 mg, 60% yield) via filtration, dried in open air and characterized by $^1H$ NMR.

Example 2

When the operation was repeated under substantially identical conditions as in EXAMPLE 1 but with the exception that 1 g of 4-acetoxybicyclo[2.2.2]octan-1-ol was used as starting material for a 4-hour reaction time, 520 mg (48% yield) of bicyclo[2.2.2]octane 1,4-dicarboxylic acid was isolated.

Example 3

When the operation was repeated under substantially identical conditions as in EXAMPLE 1 but with the exception that 1 g of bicyclo[2.2.2]octane-1,4-diol was used as starting material for a 4-hour reaction time, 1.22 g (87% yield) of bicyclo[2.2.2]octane 1,4-dicarboxylic acid was isolated.

Example 4

When the operation was repeated under substantially identical conditions as in EXAMPLE 1 but with the exception that 0.2 g of $Ag_2SO_4$ was added as catalyst for a 4-hour reaction time, the generated bicyclo[2.2.2]octane 1,4-dicarboxylic acid product is dark brown.

Example 5

Bicyclo[2.2.2]octane-1,4-dicarboxylic acid (5 g), methanol (25 mL) and several drops of 96% sulfuric acid were mixed in a 100 mL round bottom flask. The resulting suspension was stirred at 55° C. for overnight. GC-MS of the resulting clear solution indicated clean formation of dimethyl bicyclo[2.2.2]octane-1,4-dicarboxylate, which was purified via recrystallization.

Example 6

In a 100 mL stainless steel autoclave reactor, 5 g of bicyclo[2.2.2]octane-1,4-dicarboxylic acid was mixed with 50 mL of methanol. Assemble the autoclave reactor and purge with nitrogen three times to remove air. Gradually increase the temperature to 250° C. The reactor was maintained at a stirring rate of 600 rpm, a temperature of 250° C. for 5 hours. At the end of this period the reactor was cooled to room temperature. GC-MS of the resulting clear solution indicated clean formation of dimethyl bicyclo[2.2.2]octane-1,4-dicarboxylate, which was purified via recrystallization.

Example 7

10 g of copper catalyst (E406 from BASF) was packed in a stainless steel basket, which was then installed in a 100 ml autoclave (HEL). Then, the catalyst was treated in the autoclave with 1500 psig hydrogen at 200° C. for 2 hours. After the autoclave was cooled to 80° C. and the hydrogen pressure was reduced to 100 psig, 60 g of 10% dimethyl bicyclo[2.2.2]octane-1,4-dicarboxylate in n-propanol was added to the autoclave with a blowcase; thus, the reaction started. After three hours at 240° C. and 4000 psig hydrogen, the reaction was stopped, and the product was analyzed with a GC. Dimethyl bicyclo[2.2.2]octane-1,4-dicarboxylate conversion was 100% and bicyclo[2.2.2]octane-1,4-diyldimethanol selectivity was 100%.

Example 8

10 g of copper catalyst (E406 from BASF) was packed in a stainless steel basket, which was then installed in a 100 ml autoclave (HEL). Then, the catalyst was treated in the autoclave with 1500 psig hydrogen at 200° C. for 2 hours. After the autoclave was cooled to 80° C. and the hydrogen pressure was reduced to 100 psig, 60 g of 10% dimethyl bicyclo[2.2.2]octane-1,4-dicarboxylate in n-propanol was added to the autoclave with a blowcase; thus, the reaction started. After three hours at 240° C. and 2000 psig hydrogen, the reaction was stopped and the product was analyzed with a GC. Dimethyl bicyclo[2.2.2]octane-1,4-dicarboxylate conversion was 95% and bicyclo[2.2.2]octane-1,4-diyldimethanol selectivity was 92%.

Example 9

10 g of copper catalyst (E406 from BASF) was packed in a stainless steel basket, which was then installed in a 100 ml autoclave (HEL). Then, the catalyst was treated in the autoclave with 1500 psig hydrogen at 200° C. for 2 hours. After the autoclave was cooled to 80° C. and the hydrogen pressure was reduced to 100 psig, 60 g of 10% dimethyl bicyclo[2.2.2]octane-1,4-dicarboxylate in n-propanol was added to the autoclave with a blowcase; thus, the reaction started. After three hours at 200° C. and 4000 psig hydrogen, the reaction was stopped, and the product was analyzed with a GC. Dimethyl bicyclo[2.2.2]octane-1,4-dicarboxylate conversion was 99% and bicyclo[2.2.2]octane-1,4-diyldimethanol selectivity was 97%.

Example 10

At atmospheric conditions, 0.1 g of the Milstein catalyst precursor [2-(Di-tert-butylphosphinomethyl)-6-(diethylaminomethyl)pyridine]carbonylchlorohydridoruthenium(II), 30 mg of potassium hydroxide, 2.5 g of dimethyl bicyclo[2.2.2]octane-1,4-dicarboxylate and 50 mL of p-xylene were added to a 100 mL autoclave reactor. The reactor was then purged three times by pressurizing with nitrogen to 200 psig, then venting the pressure to atmospheric each time. The reactor was then purged three times by pressurizing with hydrogen to approximately 300 psig, then venting the pressure to atmospheric each time. Agitation at 800 rpm was then commenced, and hydrogen was then added to bring the pressure to 750 psig. The temperature was then increased to 140° C. while allowing pressure to rise. After the temperature reaches 140° C., the hydrogen pressure was increased to 1000 psig. These conditions (140° C. and 1000 psig) were held for 8 hours of reaction. After 8 hours of reaction, the agitation was stopped and the heat turned off to let the autoclave start cooling. After cooling to room temperature, pressure was released, and the contents were purged with nitrogen gas and vented. The solution was finally discharged from the autoclave and analyzed by GC-MS and $^1$H NMR. The conversion of dimethyl bicyclo[2.2.2]octane-1,4-dicarboxylate is 94%; the selectivity of bicyclo[2.2.2]octane-1,4-diyldimethanol is 93%; and the selectivity of methyl 4-(hydroxymethyl)bicyclo[2.2.2]octane-1-carboxylate is 7%.

Example 11

At atmospheric conditions, 0.1 g of the Milstein catalyst precursor [2-(Di-tert-butylphosphinomethyl)-6-(diethylaminomethyl)pyridine]carbonylchlorohydridoruthenium(II), 30 mg of potassium hydroxide, 2.5 g of dimethyl bicyclo[2.2.2]octane-1,4-dicarboxylate and 50 mL of p-xylene were added to a 100 mL autoclave reactor. The reactor was then purged three times by pressurizing with nitrogen to 200 psig, then venting the pressure to atmospheric each time. The reactor was then purged three times by pressurizing with hydrogen to approximately 300 psig, then venting the pressure to atmospheric each time. Agitation at 800 rpm was then commenced, and hydrogen was then added to bring the pressure to 100 psig. The temperature was then increased to 150° C. while allowing pressure to rise. After the temperature reaches 150° C., the hydrogen pressure was increased to 150 psig. These conditions (150° C. and 150 psig) were held for 8 hours of reaction. After 8 hours of reaction, the agitation was stopped, and the heat turned off to let the autoclave start cooling. After cooling to room temperature, pressure was released, and the contents were purged with nitrogen gas and vented. The solution was finally discharged from the autoclave and analyzed by GC-MS and $^1$H NMR. The conversion of dimethyl bicyclo[2.2.2]octane-1,4-dicarboxylate is 77%; the selectivity of bicyclo[2.2.2]octane-1,4-diyldimethanol is 46%; and the selectivity of methyl 4-(hydroxymethyl)bicyclo[2.2.2]octane-1-carboxylate is 54%.

Example 12

At atmospheric conditions, 0.134 g of the Ru-MACHO catalyst {Bis[2-(diphenylphosphino)ethyl]amine}carbonylchlorohydridoruthenium(II), 30 mg of potassium hydroxide, 2.5 g of dimethyl bicyclo[2.2.2]octane-1,4-dicarboxylate and 50 mL of p-xylene were added to a 100 mL autoclave reactor. The reactor was then purged three times by pressurizing with nitrogen to 200 psig, then venting the pressure to atmospheric each time. The reactor was then purged three times by pressurizing with hydrogen to approximately 300 psig, then venting the pressure to atmospheric each time. Agitation at 800 rpm was then commenced, and hydrogen was then added to bring the pressure to 750 psig. The temperature was then increased to 140° C. while allowing pressure to rise. After the temperature reaches 140° C., the hydrogen pressure was increased to 1000 psig. These conditions (140° C. and 1000 psig) were held for 8 hours of reaction. After 8 hours of reaction, the agitation was stopped, and the heat turned off to let the autoclave start cooling. After cooling to room temperature, pressure was released, and the contents were purged with nitrogen gas and vented. The solution was finally discharged from the autoclave and analyzed by GC-MS and $^1$H NMR. The conversion of dimethyl bicyclo[2.2.2]octane-1,4-dicarboxylate is 74%; the selectivity of bicyclo[2.2.2]octane-1,4-diyldimethanol is 47%; and the selectivity of methyl 4-(hydroxymethyl)bicyclo[2.2.2]octane-1-carboxylate is 53%.

Example 13

At atmospheric conditions, 0.25 g of the Ru-TRIPHOS catalyst ruthenium 1,1,1-tris(diphenylphosphinomethyl)ethane, 25 mg of p-toluenesulfonic acid, 2.5 g of dimethyl bicyclo[2.2.2]octane-1,4-dicarboxylate and 50 mL of p-xylene were added to a 100 mL autoclave reactor. The reactor was then purged three times by pressurizing with nitrogen to 200 psig, then venting the pressure to atmospheric each time. The reactor was then purged three times by pressurizing with hydrogen to approximately 300 psig, then venting the pressure to atmospheric each time. Agitation at 800 rpm was then commenced, and hydrogen was then added to bring the pressure to 1600 psig. The temperature was then increased to 200° C. while allowing pressure to rise. After the temperature reaches 200° C., the hydrogen pressure was increased to 2000 psig. These conditions (200° C. and 2000 psig) were held for 24 hours of reaction. After 24 hours of reaction, the agitation was stopped, and the heat turned off to let the autoclave start cooling. After cooling to room temperature, pressure was released, and the contents were purged with nitrogen gas and vented. The solution was finally discharged from the autoclave and analyzed by GC-MS and $^1$H NMR. The conversion of dimethyl bicyclo [2.2.2]octane-1,4-dicarboxylate is 30% and the only product methyl 4-(hydroxymethyl)bicyclo[2.2.2]octane-1-carboxylate (100% selectivity).

Example 14

At atmospheric conditions, 0.25 g of the Ru-TRIPHOS catalyst ruthenium 1,1,1-tris(diphenylphosphinomethyl)ethane, 20 mg of p-toluenesulfonic acid, 2 g of bicyclo[2.2.2] octane-1,4-dicarboxylic acid and 40 g of N-methyl-2-pyrrolidone were added to a 100 mL autoclave reactor. The reactor was then purged three times by pressurizing with nitrogen to 200 psig, then venting the pressure to atmospheric each time. The reactor was then purged three times by pressurizing with hydrogen to approximately 300 psig, then venting the pressure to atmospheric each time. Agitation at 800 rpm was then commenced, and hydrogen was then added to bring the pressure to 1600 psig. The temperature was then increased to 210° C. while allowing pressure to rise. After the temperature reaches 210° C., the hydrogen pressure was increased to 2000 psig. These conditions (210° C. and 2000 psig) were held for 6 hours of reaction. After 6 hours of reaction, the agitation was stopped, and the heat turned off to let the autoclave start cooling. After cooling to room temperature, pressure was released and the contents were purged with nitrogen gas and vented. The solution was finally discharged from the autoclave and analyzed by GC-MS and $^1$H NMR, showing bicyclo[2.2.2]octane-1,4-diyldimethanol as major product with small amount of 4-(hydroxymethyl)bicyclo[2.2.2]octane-1-carbaldehyde. The conversion of bicyclo[2.2.2]octane-1,4-dicarboxylic acid is 100%.

Example 15

At atmospheric conditions, 2 g of the product mixture that contains 4-acetoxybicyclo[2.2.2]octan-1-ol (major), 1,4-diacetoxybicyclo[2.2.2]octane (minor) and bicyclo[2.2.2]octane-1,4-diol (minor), 25 mL of methanol, 25 mL of water and 1 g of Amberlyst 70 (50% water) were added to a 100 mL autoclave reactor. The reactor was then purged three times by pressurizing with nitrogen to 200 psig, then venting the pressure to atmospheric each time. Agitation at 800 rpm was then commenced, and the temperature was increased to 180° C. while allowing pressure to rise. These conditions (180° C. and 800 rpm) were held for 4 hours of reaction. After 4 hours of reaction, the agitation was stopped, and the heat turned off to let the autoclave start cooling. After cooling to room temperature, pressure was released, and the contents were analyzed by GC-MS and $^1$H NMR. Both 4-acetoxybicyclo[2.2.2]octan-1-ol and 1,4-diacetoxybicyclo [2.2.2]octane were converted cleanly to bicyclo[2.2.2]octane-1,4-diol.

The above reaction can also be catalyzed by other transesterification catalysts, including but not limited to inorganic acids (e.g. sulfuric acid, hydrogen chloride), inorganic bases (e.g. NaOH, KOH), transition metal complexes (e.g. Sn, Ti), and other solid acids and bases.

Example 16

In a 25 mL round bottom flask, 2 g of the product mixture contains 4-acetoxybicyclo[2.2.2]octan-1-ol (major), 1,4-diacetoxybicyclo[2.2.2]octane (minor) and bicyclo[2.2.2]octane-1,4-diol (minor) was mixed with 10 mL acetic anhydride and 0.5 mL pyridine. The resulting mixture was stirred at 100 Celsius for 4 hours and cooled to room temperature. The solution after filtration was analyzed by GC-MS. Both 4-acetoxybicyclo[2.2.2]octan-1-ol and bicyclo[2.2.2]octane-1,4-diol were converted cleanly to 1,4-diacetoxybicyclo[2.2.2]octane.

Example 17

In a 25 mL thick-wall glass tube equipped with a ⅛ magnetic stir bar, 1 g of 1,4-diacetoxylbicyclo[2.2.2]octane was mixed with 1 g of potassium bromide (1 g), and 5 g of 100% $H_3PO_4$ (made from 85% $H_3PO_4$ and $P_2O_5$). The resulting mixture was stirred at 100° C. for 4 hours. After cooling the mixture was quenched with 10 g ice water and extracted with diethyl ether. The extract was washed with saturated aqueous $NaHCO_3$, water and brine. GC-MS of the ether solution showed bicyclo[2.2.2]octane-1,4-dibromide as the major product. After drying ($MgSO_4$) and evaporation of the solvent the raw bicyclo[2.2.2]octane-1,4-dibromide was purified by sublimation, crystallization or column chromatography.

Example 18

At atmospheric conditions, 2 g of bicyclo[2.2.2]octane-1,4-diyldimethanol, 40 Ml of p-xylene, and 2 g of Raney Nickel 3200 were added to a 100 mL autoclave reactor. The reactor was then purged with 300 psig of nitrogen, then venting the pressure to atmospheric. Condense 15 g of ammonia gas to a blowcase and use 300 psig of $N_2$ to push the ammonia to the autoclave. Agitation at 800 rpm was then commenced, and the temperature was slowly increased to 250° C. while allowing pressure to rise. Bring the reactor pressure down to 2800-2900 psig if pressure exceeds 3000 psig. After the temperature reaches 250° C., hold these conditions (250° C. and 2000 psig) for 8 hours.

After 8 hours of reaction, the agitation was stopped, and the heat turned off to let the autoclave start cooling. After cooling to room temperature, pressure was released, and the system was purged three times with 100 psig of nitrogen. Vent the autoclave and discharge the reaction mixture from the autoclave and analyze by GC-MS and 1H NMR, showing bicyclo[2.2.2]octane-1,4-diyldimethanamine as major product with small amount of 4-(aminomethyl)bicyclo [2.2.2]octane-1-carbaldehyde. The conversion of bicyclo [2.2.2]octane-1,4-diyldimetanol is 100%.

Comparative Example 1

When the operation was repeated under substantially identical conditions but with the exception that 20 cc of 96% sulfuric acid and 500 psig carbon monoxide were used for a 4-hour reaction time, no detectable amount of bicyclo[2.2.2]octane 1,4-dicarboxylic acid was observed after the reaction.

Comparative Example 2

25 cc of orthophosphoric acid (prepared from 85% phosphoric acid and P$_2$O$_5$) and 1 g of 1,4-diacetoxybicyclo[2.2.2]octane were charged to a 100 mL stainless steel autoclave reactor equipped with glass liner. The assembled autoclave reactor was pressurized with carbon monoxide to 500 psig pressure. The reaction temperature was increased to 140° C. The reactor was maintained at a stirring rate of 600 rpm, a temperature of 140° C. and a pressure of 500 psig for 5 hours. At the end of this period, the reactor was cooled to room temperature and the pressure was reduced to atmospheric by cutting off the source of carbon monoxide and venting. The reaction mixture was then diluted with 100 cc water; care being taken to maintain the temperature below about 30° C. throughout the dilution. Dilution of the reaction mixture resulted in the formation of unidentified brown precipitates. No bicyclo[2.2.2]octane 1,4-dicarboxylic acid was observed from the reaction.

Comparative Example 3

30 cc of trifluoroacetic acid and 1 g of 1,4-diacetoxybicyclo[2.2.2]octane were charged to a 100 mL Ti autoclave reactor. The assembled autoclave reactor was pressurized with carbon monoxide to 2000 psig pressure. The reaction temperature was increased to 140° C. The reactor was maintained at a stirring rate of 600 rpm, a temperature of 140° C. and a pressure of 2000 psig for 4 hours. At the end of this period, the reactor was cooled to room temperature and the pressure was reduced to atmospheric by cutting off the source of carbon monoxide and venting. After removing trifluoroacetic acid, the resulting solid was identified as bicyclo[2.2.2]octane-1,4-diyl bis(2,2,2-trifluoroacetate). No bicyclo[2.2.2]octane 1,4-dicarboxylic acid was observed from the reaction.

We claim:
1. A process comprising contacting a compound of the formula

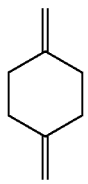

with (i) a transition metal catalyst comprising a palladium compound and (ii) an oxidizing agent;
optionally in the presence of at least one of
(I) a compound of the formula

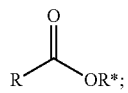

wherein R is chosen from hydrogen; and C$_1$-C$_{12}$ alkyl, optionally substituted by one or more of groups chosen from C$_1$-C$_6$ alkoxy, halo, nitro, and cyano;

and wherein R* is chosen from hydrogen; C$_1$-C$_{12}$ alkyl, optionally substituted by one or more of groups chosen from C$_1$-C$_6$ alkoxy, halo, nitro, and cyano; and an alkali metal cation;
or
(II) a compound having at least one C$_1$-C$_{12}$ alkanoyloxy moiety of the formula

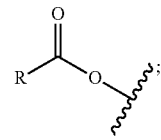

wherein R is chosen from C$_1$-C$_{12}$ alkyl, optionally substituted by one or more of groups chosen from C$_1$-C$_6$ alkoxy, halo, nitro, and cyano;
to afford a compound of the formula

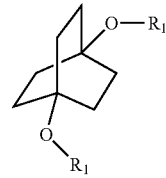

(I)

wherein each R$_1$ is independently hydrogen or a group of the formula

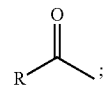

wherein R is C$_1$-C$_{12}$ alkyl, optionally substituted by one or more of groups chosen from C$_1$-C$_6$ alkoxy, halo, nitro, and cyano;
further comprising a step chosen from (a), (b), or (c):
(a) the step of reaction with carbon monoxide in the presence of a strong acid, followed by quenching with at least one of (i) water or (ii) an alcohol of the formula R—OH, to afford compounds of the formula

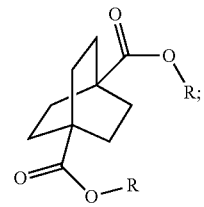

wherein R is chosen from hydrogen; and C$_1$-C$_{12}$ alkyl, optionally substituted by one or more of groups chosen from C$_1$-C$_6$ alkoxy, halo, nitro, and cyano;
optionally further comprising the step of:
contacting with hydrogen in the presence of a heterogeneous copper hydrogenation catalyst or a homogeneous hydrogenation catalyst to afford a compound of the formula

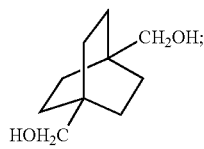

optionally followed by reductive amination to afford a compound of the formula

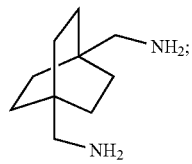

(b) the step of conversion to a compound of the formula:

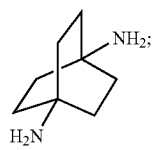

which comprises reaction of (I) with a nitrile in the presence of an acid followed by hydrolysis to the corresponding amine;

optionally further comprising treatment of said corresponding amine with phosgene (COCl$_2$) to afford a compound of the formula:

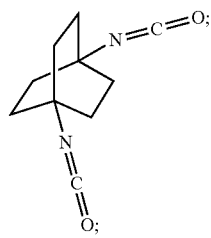 [SMILES: O=C=NC12CCC(N=C=O)(CC1)CC2]

or (c) the step of halogenation of (I) to afford a compound of the formula:

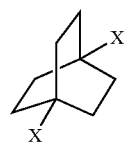

wherein X is halo;

optionally further comprising a step chosen from:

a. reaction with carbon monoxide in the presence of a strong acid, followed by quenching with at least one of (i) water or (ii) an alcohol of the formula R—OH, to afford compounds of the formula

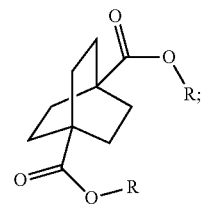

wherein R is chosen from hydrogen; and C$_1$-C$_{12}$ alkyl, optionally substituted by one or more of groups chosen from C$_1$-C$_6$ alkoxy, halo, nitro, and cyano;

b. amination via treatment with ammonia to afford a compound of the formula:

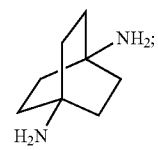

or b. hydroformylation via treatment with carbon monoxide and hydrogen in the presence of at least one of a cobalt or ruthenium catalyst at a temperature of about 90 to 250° C. and a pressure of about 5 to 300 bar, to afford a compound of the formula:

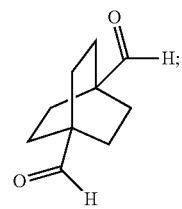

optionally further comprising:

a. treatment with an oxidizing agent, optionally in the presence of a homogeneous and/or heterogeneous catalyst to afford a compound of the formula:

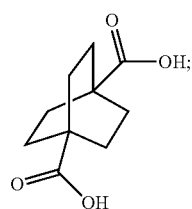 [SMILES: O=C(O)C12CCC(C(=O)O)(CC1)CC2]

or b. hydrogenation in the presence of a homogeneous and/or heterogeneous catalyst to afford a compound of the formula:

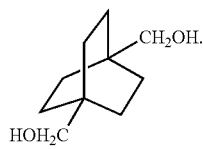

2. The process of claim 1, represented by step (a).

3. The process of claim 2, further comprising contacting with hydrogen in the presence of a heterogeneous copper hydrogenation catalyst or a homogeneous hydrogenation catalyst to afford a compound of the formula

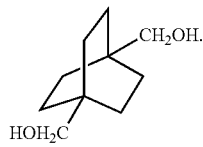

4. The process of claim 3, further comprising reductive amination to afford a compound of the formula

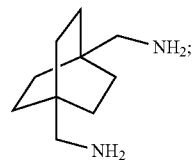

5. The process of claim 2, further comprising one of the following steps:
(i) formation of an ammonium salt, followed by the application of heat;
(ii) formation of an acid halide, followed by treatment with ammonia; or
(ii) formation of an anhydride, followed by treatment with ammonia;
to afford a compound of the formula

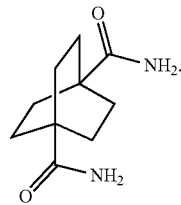

6. The process of claim 5, further comprising hydrogenation in the presence of a catalyst, to afford a compound of the formula

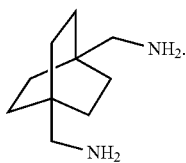

7. The process of claim 1, represented by step (b).

8. The process of claim 7, further comprising treatment of the corresponding amine with phosgene ($COCl_2$) to afford a compound of the formula:

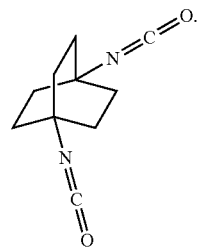 [SMILES: O=C=NC12CCC(N=C=O)(CC1)CC2]

9. The process of claim 1, represented by step (c).

10. The process of claim 9, further comprising reaction with carbon monoxide in the presence of a strong acid, followed by quenching with at least one of (i) water or (ii) an alcohol of the formula R—OH, to afford compounds of the formula:

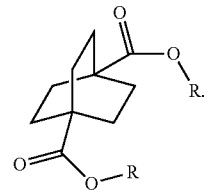

wherein R is chosen from hydrogen; and $C_1$-$C_{12}$ alkyl, optionally substituted by one or more of groups chosen from $C_1$-$C_6$ alkoxy, halo, nitro, and cyano.

11. The process of claim 9, further comprising amination via treatment with ammonia to afford a compound of the formula:

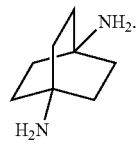

12. The process of claim 9, further comprising hydroformylation via treatment with carbon monoxide and hydrogen in the presence of a ruthenium catalyst at a temperature of about 90 to 250° C. and a pressure of about 5 to 300 bar, to afford a compound of the formula:

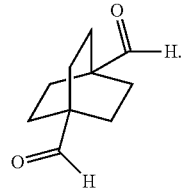

13. The process of claim 12, further comprising treatment with an oxidizing agent to afford a compound of the formula:

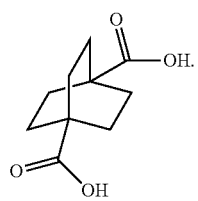

14. The process of claim 12, further comprising hydrogenation in the presence of a catalyst, to afford a compound of the formula:

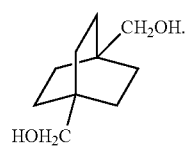

15. A process for preparing a compound of the formula

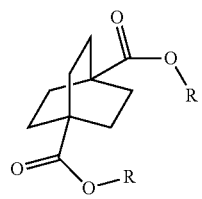

wherein R is independently hydrogen; or $C_1$-$C_{12}$ alkyl, optionally substituted by one or more of groups chosen from $C_1$-$C_6$ alkoxy, halo, nitro, and cyano; or phenyl, optionally substituted by one or more of groups chosen from $C_1$-$C_6$ alkoxy, halo, nitro, cyano, and $C_1$-$C_{12}$ alkyl;

which comprises reaction of the compound of the formula

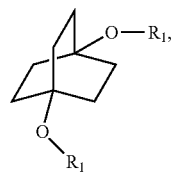

wherein each $R_1$ is independently hydrogen or a group of the formula

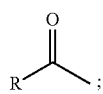

wherein R is independently hydrogen; or $C_1$-$C_{12}$ alkyl, optionally substituted by one or more of groups chosen from $C_1$-$C_6$ alkoxy, halo, nitro, and cyano; or phenyl, optionally substituted by one or more of groups chosen from $C_1$-$C_6$ alkoxy, halo, nitro, cyano, and $C_1$-$C_{12}$ alkyl;

with carbon monoxide in the presence of a strong acid, followed by quenching with at least one of (i) water or (ii) an alcohol of the formula R—OH; wherein R is independently hydrogen; or $C_1$-$C_{12}$ alkyl, optionally substituted by one or more of groups chosen from $C_1$-$C_6$ alkoxy, halo, nitro, and cyano; or phenyl, optionally substituted by one or more of groups chosen from $C_1$-$C_6$ alkoxy, halo, nitro, cyano, and $C_1$-$C_{12}$ alkyl.

16. A process for preparing a compound of the formula

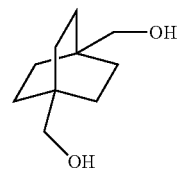

which comprises contacting a compound of the formula

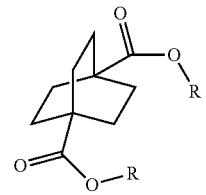

wherein R is $C_1$-$C_6$ alkyl, with hydrogen in the presence of a homogeneous ruthenium catalyst.

17. A process for preparing a compound of the formula

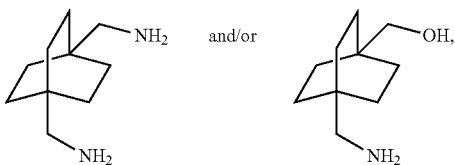 [SMILES: NCC12CCC(CN)(CC1)CC2 ; NCC12CCC(CO)(CC1)CC2]

which comprises subjecting a compound of the formula:

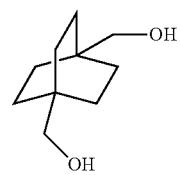

to reductive amination.

18. A process for preparing a compound of the formula

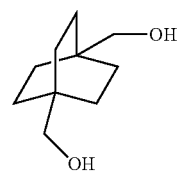

which comprises contacting a compound of the formula
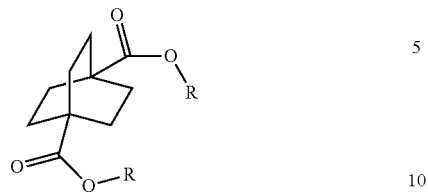
wherein R is chosen from hydrogen; and $C_1$-$C_{12}$ alkyl, optionally substituted by one or more of groups chosen from $C_1$-$C_6$ alkoxy, halo, nitro, and cyano; with hydrogen in the presence of a homogeneous hydrogenation catalyst.
* * * * *